(12) United States Patent
Rosenfeld et al.

(10) Patent No.: US 7,475,019 B2
(45) Date of Patent: *Jan. 6, 2009

(54) SYSTEM AND METHOD FOR PHYSICIAN NOTE CREATION AND MANAGEMENT

(75) Inventors: Brian Rosenfeld, Baltimore, MD (US); Michael Breslow, Lutherville, MD (US)

(73) Assignee: Visicu, Inc., Baltimore, MD (US)

( * ) Notice: Subject to any disclaimer, the term of this patent is extended or adjusted under 35 U.S.C. 154(b) by 318 days.

This patent is subject to a terminal disclaimer.

(21) Appl. No.: 10/654,668

(22) Filed: Sep. 4, 2003

(65) Prior Publication Data

US 2004/0111296 A1     Jun. 10, 2004

Related U.S. Application Data

(63) Continuation-in-part of application No. 09/443,072, filed on Nov. 18, 1999, now Pat. No. 6,804,656.

(51) Int. Cl.
   *G06Q 10/00*     (2006.01)
(52) U.S. Cl. .................. 705/2; 705/3; 600/300
(58) Field of Classification Search ................. 705/2–3; 600/300
   See application file for complete search history.

(56) References Cited

U.S. PATENT DOCUMENTS

| | | | |
|---|---|---|---|
| 3,646,606 A * | 2/1972 | Buxton et al. ............... | 600/483 |
| 4,365,199 A | 12/1982 | McNair | |
| 4,489,387 A | 12/1984 | Lamb et al. | |
| 4,731,725 A | 3/1988 | Suto et al. | |
| 4,838,275 A | 6/1989 | Lee | |
| 4,852,570 A * | 8/1989 | Levine ....................... | 600/301 |
| 4,878,175 A | 10/1989 | Norden-Paul et al. | |
| 5,255,187 A | 10/1993 | Sorensen | |
| 5,296,688 A * | 3/1994 | Hamilton et al. ............ | 235/375 |
| 5,321,800 A | 6/1994 | Lesser | |
| 5,348,008 A | 9/1994 | Bornn et al. | |

(Continued)

FOREIGN PATENT DOCUMENTS

WO     WO 98/29790     7/1998

(Continued)

OTHER PUBLICATIONS

Terry Ann Capuano et al. Remote Telemetry, Jul. 1995, Nursing Management, vol. 26, No. 7, p. 26.*

(Continued)

*Primary Examiner*—Robert W Morgan
(74) *Attorney, Agent, or Firm*—Roberts, Mardula & Wertheim, LLC

(57) ABSTRACT

The present invention is a system and method for inputting physician notes associated with the admission, diagnosis and treatment of patients in a healthcare system. It can be used for those who are critically ill as well as those who are engaged in more routine medical care. The present invention reduces the risk of medical treatment by populating specific patient information throughout the patient care system so that current physician notes are combined with other information and made available rapidly to hospital personnel at all levels of patient care. The present invention also assists in analyzing data in relation to risk associated with management choices and managing the patient care to reduce assessed risk.

25 Claims, 23 Drawing Sheets

U.S. PATENT DOCUMENTS

| | | | |
|---|---|---|---|
| 5,544,649 A | 8/1996 | David et al. | |
| 5,544,661 A | 8/1996 | Davis et al. | |
| 5,574,828 A | 11/1996 | Hayward et al. | |
| 5,576,952 A | 11/1996 | Stutman et al. | |
| 5,619,991 A | 4/1997 | Sloane | |
| 5,678,562 A | 10/1997 | Sellers | |
| 5,701,894 A | 12/1997 | Cherry et al. | |
| 5,715,449 A | 2/1998 | Peters, Jr. et al. | |
| 5,724,580 A | 3/1998 | Levin et al. | |
| 5,729,204 A | 3/1998 | Fackler et al. | |
| 5,772,585 A * | 6/1998 | Lavin et al. | 600/300 |
| 5,812,983 A | 9/1998 | Kumagai | |
| 5,822,544 A | 10/1998 | Chaco et al. | |
| 5,823,948 A | 10/1998 | Ross, Jr. et al. | |
| 5,832,450 A | 11/1998 | Myers et al. | |
| 5,839,438 A | 11/1998 | Graettinger et al. | |
| 5,842,978 A | 12/1998 | Levy | |
| 5,867,821 A | 2/1999 | Ballantyne et al. | |
| 5,868,669 A | 2/1999 | Iliff | |
| 5,899,855 A | 5/1999 | Brown | |
| 5,924,074 A * | 7/1999 | Evans | 705/3 |
| 5,942,986 A | 8/1999 | Shabot et al. | |
| 5,987,519 A | 11/1999 | Peifer et al. | |
| 6,024,699 A | 2/2000 | Surwit et al. | |
| 6,093,146 A | 7/2000 | Filangeri | |
| 6,102,856 A | 8/2000 | Groff et al. | |
| 6,154,668 A | 11/2000 | Pedersen et al. | |
| 6,168,563 B1 | 1/2001 | Brown | |
| 6,215,403 B1 | 4/2001 | Chan et al. | |
| 6,225,901 B1 | 5/2001 | Kail, IV | |
| 6,230,142 B1 | 5/2001 | Begnino et al. | |
| 6,234,964 B1 | 5/2001 | Iliff | |
| 6,238,338 B1 | 5/2001 | DeLuca et al. | |
| 6,245,013 B1 | 6/2001 | Minoz et al. | |
| 6,254,536 B1 | 7/2001 | DeVito | |
| 6,278,999 B1 | 8/2001 | Knapp | |
| 6,292,698 B1 | 9/2001 | Duffin et al. | |
| 6,304,788 B1 | 10/2001 | Eady et al. | |
| 6,315,719 B1 | 11/2001 | Rode et al. | |
| 6,338,039 B1 * | 1/2002 | Lonski et al. | 705/3 |
| 6,364,834 B1 | 4/2002 | Reuss et al. | |
| 6,385,589 B1 | 5/2002 | Trusheim et al. | |
| 6,398,728 B1 | 6/2002 | Bardy | |
| 6,442,433 B1 | 8/2002 | Linberg | |
| 6,533,724 B2 | 3/2003 | McNair | |
| 6,741,264 B1 | 5/2004 | Lesser | |
| 6,835,176 B2 | 12/2004 | McNair | |
| 6,893,396 B2 | 5/2005 | Schulze et al. | |
| 2002/0002473 A1 | 1/2002 | Schrier et al. | |
| 2002/0177758 A1 | 11/2002 | Schoenberg et al. | |
| 2002/0177759 A1 | 11/2002 | Schoenberg et al. | |
| 2002/0187483 A1 | 12/2002 | Hoffman et al. | |
| 2002/0193667 A1 | 12/2002 | McNair | |
| 2003/0036687 A1 | 2/2003 | Schoenberg et al. | |
| 2004/0030578 A1 | 2/2004 | Cross et al. | |
| 2004/0063031 A1 | 4/2004 | Gallucci et al. | |
| 2004/0078366 A1 | 4/2004 | Crooks et al. | |
| 2004/0193451 A1 | 9/2004 | McNair | |
| 2004/0197813 A1 | 10/2004 | Hoffman et al. | |
| 2004/0199333 A1 | 10/2004 | Hoffman et al. | |
| 2004/0225201 A1 | 11/2004 | McNair | |
| 2004/0236604 A1 | 11/2004 | McNair | |
| 2005/0027563 A1 | 2/2005 | Fackler et al. | |
| 2005/0049891 A1 | 3/2005 | Wilson | |
| 2005/0060191 A1 | 3/2005 | Parkins et al. | |
| 2005/0075794 A1 | 4/2005 | Hoffman et al. | |
| 2005/0075904 A1 | 4/2005 | Wagner et al. | |
| 2005/0076060 A1 | 4/2005 | Finn et al. | |
| 2005/0125098 A1 | 6/2005 | Wang et al. | |
| 2005/0125256 A1 * | 6/2005 | Schoenberg et al. | 705/2 |
| 2005/0208518 A1 | 9/2005 | Welch et al. | |
| 2005/0228241 A1 | 10/2005 | McNair | |
| 2005/0251418 A1 | 11/2005 | Fox, Jr. et al. | |
| 2005/0267351 A1 | 12/2005 | Humphrey et al. | |
| 2005/0283062 A1 | 12/2005 | Hoffman et al. | |
| 2006/0031018 A1 | 2/2006 | Bush et al. | |
| 2006/0036542 A1 | 2/2006 | McNair | |

FOREIGN PATENT DOCUMENTS

| | | |
|---|---|---|
| WO | WO 99/13766 | 3/1999 |
| WO | 00/79466 A2 | 12/2000 |

OTHER PUBLICATIONS

Grundy, Betty Lou; Jones, Paul; Lovitt, Ann; "Telemedicine in critical care: Problems in design, implementation and assessment" Jul. 1982. Critical Care Medicine vol. 10, No. 7.

Editors: M. Michael Shabot and Reed M. Gardner, Computers and Medicine: Decision Support Systems in Critical Care, 1994, Springer-Verlag New York, Inc. New York.

Gilad J. Kuperman, M.D. and Reed M. Gardner, Ph.D., The Help System: A Snapshot in Time, 1988, Dept. of Biophysics, LDS Hospital, Salt Lake City, Utah.

Project Leaders: Benoit Dawant, Ph.D. and John A. Morris, Jr. M.D., Vanderbilt University Simon Project Website, 2004, Vanderbilt University, Nashville, Tennessee.

Greg Borzo, Web Technology: Coming Soon to a Hospital Near You, American Medical News, Nov. 18, 1996, American Medical Association www.amednews.com.

Abstract: J.E. Gray, C. Safran, R.B. Davis, G. Pomilio-Weitzner, J.E. Stewart, L. Zaccagnini and D. Pursley, Baby Care Link: Using the Internet and Telemedicine to Improve Care for High-risk Infants, Dec. 2000, Pediatrics, vol. 106, No. 6, pp. 1318-1324.

Abstract: Ray Duncan and Jeffrey J. Pomerance, Computer Assistance in Delivery of Patient Care in a Neonatal Intensive Care Unit, The Use of Computers in Perinatal Medicine, Chapter 19, pp. 337-351, 1982, Praeger Publishers, New York, NY.

Abstract: Ray Duncan, MD, Computer Assisted Care in the Neonatal Intensive Care Unit, Proceedings of the 17th Annual Symposium on Computer Applications in Medical Care, Nov. 1993, p. 929, American Medical Informatics Association.

Abstract: Metnitz PG, Laback P. Popow C, Laback 0, Lenz K, Hiesmayr M, Computer assisted data analysis in intensive care: the ICDEV project—development of a scientific database system for intensive care (Intensive Care Data Evaluation Project), International Journal of Clinical Monitoring and Computing, 1995, vol. 12, No. 3, pp. 147-159.

Abstract: Paul H. Peristein, MD, Neil K. Edwards, MS, Harry D. Atherton, MS, James M. Sutherland, MD, Computer Assisted Newborn Intensive Care, Pediatrics, Apr. 1976, vol. 57, No. 4, pp. 494-501.

Abstract: Edward H. Shortliffe, MD, PHD, Computer Programs to Support Clinical Decision Making, Jama, Jul. 3, 1987, vol. 258, No. 1, pp. 61-66.

Abstract: Merz U, Peschgens T, Budde R, Kretzschmann F, Homchen H V, Computer-assisted monitoring in the neonatal intensive care unit [German], Klin Padiatr, Nov./Dec. 1995, vol. 207, No. 6, pp. 331-333.

Abstract: Charles Safran, MD, Francois Herrman, MD, David Rind, MD, Hollis B. Kowaloff, BA, Howard L. Bleich, MD, and Warner V. Slack, MD, Computer-Based Support for Clinical Decision Making, M.D. Computing, 1990, vol. 7, No. 5, pp. 319-322.

Abstract: Reed M. Gardner, PHD, Computerized Management of Intensive Care Patients, M.D. Computing, 1986, vol. 3, No. 1, pp. 36-51.

Abstract: F. John Lewis; Steven Deller; Michael Quinn; Benjamin Lee; Raymond Will; and John Raines, Continuous Patient Monitoring with a Small Digital Computer, Computers and Biomedical Research, 1972, vol. 5, pp. 411-428.

Abstract: N. Fumai, C. Collet, M. Petroni, K. Roger, A. Lam, E. Saab, A.'S. Malowany, F. A. Carnevale, R. D. Gottesman, Database Design of an Intensive Care Unit Patient Data Management System, Proceedings of the Fourth Annual IEEE Symposium on Computer-Based Medical Systems, May 12, 1991, pp. 78-85, IEEE Computer Society Press, Los Alamitos, CA.

Abstract: George Hripcsak; Paul D. Clayton; Robert A. Jenders; James J. Cimino; and Stephen B. Johnson, Design of a Clinical Event Monitor, Computers and Biomedical Research, Jun. 1996, vol. 29, No. 3, pp. 194-221.

Abstract: David M. Rind, MD; Roger Davis, SCD; and Charles Safran, MD, Designing Studies of Computer-Based Alerts and Reminders, MD Computing, 1995, vol. 12, No. 2, pp. 122-126.

Abstract: Dwayne R. Westenkow, PHD, Automating Patient Care with Closed-Loop Control, M.D. Computing, 1986, vol. 3, No. 2, pp. 14-20.

Abstract: Snowden S, Brownlee KG, Dear PR, An expert system to assist neonatal intensive care, I Med Eng Technol Mar.-Apr. 21, 1997;(2):67-73, vol. 21, No. 2, pp. 67-73.

Abstract: A. Aifredo Morales, Engr., MS , James Gray, MD, MS , Charles Safran, MD, An Application Server Approach for Integration of Clinical Systems, Proceedings of the AMIA 1999 Annual Symposium, 1999, AMIA.

Abstract: Kang Wang, PHD; Isaac Kohane, MD, PHD; Karen L. Bradshaw, BS; James Facider, MD, A Real Time Patient Monitoring System on the World Wide Web, Proceedings of the 1996 AMIA Annual Fall Symposium, Nov. 1996, pp. 729-732, Hanley and Belfus, Inc.

Abstract: Michael Factor, David H. Gelernter, Craig E. Kolb, Perry L. Miller and Dean F. Sittig, Real-Time Data Fusion in the Intensive Care Unit, IEEE Computer, Nov. 1991, pp. 45-53.

Editor: Judy G. Ozbolt, Ph.D., A Conference of the American Medical Informatics Association, Symposium on Computer Applications in Medical Care, Nov. 5-9, 1994, Hanley & Belfus, Inc. Medical Publishers, Philadelphia, PA.

W. Hsueh-Fen Young, Reed M. Gardner, Thomas D. East and Kristi Turner, Computerized Ventilator Data Selection: Artifact Rejection and Data Reduction, Int'l Journal of Clinical Monitoring and Computing 1997, 14: 165-176, Kluwer Academic Publishers, Netherlands.

Randolph A. Miller, M.D. and Reed M. Gardner, Ph.D., Summary Recommendations for Responsible Monitoring and Regulation of Clinical Software Systems, Annals of Internal Medicine, Nov. 1997, vol. 127, No. 9.

Reed M. Gardner, T. Allan Pryor and Homer R. Warner, The HELP Hospital Information System: Update 1998, Intl Journal of Medical Informatics 1999, vol. 54, pp. 169-182, Elsevier Science Ireland Ltd., Ireland.

Martin Spikoff, Systems Aid Rural Health Delivery, QIPhysician.com, Sep. 2003.

Abstract: Jerome P. Kassirer, MD, The Next Transformation in the Delivery of Health Care (Editorial), NEJM, Jan. 5, 1995, vol. 332, No. 1, pp. 52-54.

Abstract: Lorene S. Avila; M. Michael Shabot, keys to the successful implementation of an ICU patient data management system, International Journal of Clinical Monitoring and Computing, 1988, vol. 5, pp. 15-25.

Abstract: Reed M. Gardner, MD; M. Michael Shabot, MD, Computerized ICU Data Management: Pitfalls and Promises, International Journal of Clinical Monitoring and Computing, 1990, vol. 7, pp. 99-105.

Karl W. Thomas, M.D., Charles S. Dayton, B.S., R.Ph., and Michael W. Peterson, M.D., Evolution of Internet-Based Clinical Decision Support Systems, Journal of Medical Internet Research 1999, vol. 1, University of Iowa, Iowa City, Iowa.

Abstract: C. J. McDonald, Protocol-Based Computer Reminders, The Quality of Care and The Non-Perfectability of Man, The New England Journal of Medicine, Dec. 9, 1976, vol. 295, No. 24, 1351-1355.

Abstract: T.D. East, A.H. Morris, C.J. Wallace, T.P. Clemmer, J.F. Orme, Jr., L.K. Weaver, S. Henderson and D.F. Sittig, A Strategy for Development of Computerized Critical Care Decision Support Systems, Intl Journal of Clinical Monitoring and Computing, 1991-92, vol. 8, No. 4, 263-269.

Dr. Ramana Reddy and Dr. V. "Juggy" Jagannathan, Secure Collaboration Technology for Rural Clinical Telemedicine, National Library of Medicine, Oct. 8, 1996 Press Release, West Virginia University, West Virginia.

West Virginia University Research Corporation, Secure Collaboration Technology for Rural Clinical Telemedicine: Final Report, National Library of Medicine.

Martin J. Tobin, M.D., Principles and Practice of Intensive Care Monitoring, 1998, McGraw-Hill Inc.

Peter J. Haug, Reed M. Gardner, and R. Scott Evans, "Hospital-Based Decision Support" in *Clinical Decision Support Systems: Theory and Practice*, Eta S. Berner [ed.], 1999, Springer-Verlag New York, Inc., New York, NY, pp. 77-103.

Clement J. McDonald, M.D. and William M. Tierney, M.D., Computer-Stored Medical Records: Their Future Role in Medical Practice, JAMA, Jun. 17, 1988, pp. 3433-3440, vol. 259, No. 23.

Gilad J. Kuperman, Reed M. Gardner, and T. Allan Pryor, Help: A Dynamic Hospital Information System, 1991, Springer-Verlag New York, Inc., New York, NY.

M. Michael Shabot, M.D., Mark Lobue, B.S., and Jeannie Chen, Pharm.D., Wireless Clinical Alerts for Physiologic, Laboratory and Medication Data, Department of Enterprise Information Services, Surgery and Pharmacy Cedars-Sinai Health System, Los Angeles, CA.

Chaoxin Sima, Ravi Raman, Ramana Reddy, William Hunt and Sumitra Reddy, Vital Signs Services for Secure Telemedicine Applications, Concurrent Engineering Research Center, West Virginia University, Morgantown, WV.

Dickey Seidlitz Johnson, Jane Ranzenberger, Ruth D. Herbert, Reed M. Gardner, and Terry P. clemmer, A Computerized Alert Program for Acutely Ill Patients, Journal of Nursing Administration, Jun. 1980, pp. 26-35.

Reed M. Gardner, Ph.D., Blair J. West, M.S., T. Allan Pryor, Ph.D., Keith G Larsen, R.Ph., Homer R Warner, M.D., Terry P Clemmer, M.D., James F. Orme, Jr. M.D., Computer-Based ICU Data Acquisition as an Aid to Clinical Decision-Making, Critical Care Medicine, 1982, pp. 823-830, vol. 10, No. 12, The Williams & Wilkins Co.

Reed M. Gardner and Terry P. Clemmer, Computerized Protocols Applied to Acute Patient Care, 1977, Mediad Inc., Tarrytown, NY.

Karen E. Bradshaw, Reed M. Gardner, and T. Allan Pryor, Development of a Computerized Laboratory Alerting System, Computers and Biomedical Research 22, 575-587, 1989, Academic Press, Inc.

Terry P. Clemmer and Reed M. Gardner, Medical Informatics in the Intensive Care Unit: State of the Art 1991, International Journal of Clinical Monitoring and Computing 8: 237-250, 1992, Kluwer Academic Publishers, Netherlands.

Reed M. Gardner, Ph.D., David V. Ostler, and O. Hank Duffy, M.D., Computers in the Emergency Room, Internal Medicine for the Specialist, vol. 8, No. 3, Mar. 1987.

Dean F. Sittig, Nathan L. Pace, Reed M. Gardner, Eduardo Beck, and Alan H. Morris, Implementation of a Computerized Patient Advice System Using the HELP Clinical Information System, Computers and Biomedical Research 22, 474-487, 1989, Academic Press Inc.

P. D. Clayton, R. Scott Evans, T. Pryor, R. M. Gardner, P. J. Haug, O. B. Wigertz, and H. R. Warner, Bringing HELP to the Clinical Laboratory—Use of an Expert System to Provide Automatic Interpretation of Laboratory Data, Ann Clin Biochem 1987; 24: Supplement.

D. F. Sittig, Ph.D., R. M. Gardner, Ph.D., N. L. Pace, M.D., M. Bombino, M. D., and A. H. Morris, M.D., Compas: A Computerized Patient Advice System to Direct Ventilatory Care, Medical Informatics 88: Computers in Clinical Medicine, Sep. 13-15, 1988, British Medical Informatics Society, London.

Karen E. Bradshaw, Ph.D., Dean F. Sittig, Ph.D., Reed M. Gardner, Ph.D., T. Allan Pryor, Ph.D., and Marge Budd, M.S., Improving Efficiency and Quality in a Computerized ICU, 1988 SCAMC, Inc.

Dean F. Sittig, Ph.D., C. Gregory Elliott, M.D., C. Jane Wallace, R.N., B.S.N., Polly Bailey, R.N., Reed M. Gardner, Ph.D., Computerized Screening for Identification of Adult Respiration Distress Syndrome (ARDS) Patients, 1988 SCAMC, Inc.

R. Scott Evans, Ph.D., Reed M. Gardner, Ph.D., John P. Burke, M.D., Stanley L. Pestotnik, R.P.H., Robert A. Larsen, M.D., David C.

Classen, M.D., and Paul D. Clayton, Ph.D., A Computerized Approach to Monitor Prophylactic Antibiotics, 1987, SCAMC, Inc.

Susan Henderson, B.A., Thomas D. East, Ph.D., Alan H. Morris, M.D., Reed M. Gardner, Ph.D., Performance evaluation of computerized clinical protocols for management of arterial hypoxemia in ARDS patients, LDS Hospital, and University of Utah, Salt Lake City, UT.

Thomas D. East, Ph.D., Susan Henderson, B.A., Alan H. Morris, M.D., Reed M. Gardner, Ph.D., Implementation Issues and Challenges for Computerized Clinical Protocols for Management of Mechanical Ventilation in ARDS Patients, LDS Hospital, Salt Lake City, UT.

C. Gregory Elliott, M.D., Deon Simmons, R.R.T., C. Duwayne Schmidt, M.D., Kip Enger, B.S., C.R.T.T., Loren Greenway, B.S., R.R.T., and Reed M. Gardner, Ph.D., Computer-Assisted Medical Direction of Respiratory Care, Respiratory Management, vol. 19, No. 2.

H. Keller and CH. Trendelenburg, Data Presentation Interpretation, Clinical Biochemistry Principles, Methods, Applications, WalterdeGruyter & Co., 1989.

Reed M. Gardner, Ph.D., Karen W. Hollingsworth, R.N., M.S, C.C. R.N., ECG and Pressure Monitoring: How to Obtain Optimal Results, 295-305.

Reed M. Gardner, Ph.D., Dean F. Sittig, M.S., Marge C. Budd, R.N., M.S., Computers in the Intensive Care Unit: Match or Mismatch?, 248-259.

Emmanuel Furst, Ph.D., Cardiovascular Technology, The Journal of Cardiovascular Nursing, Nov. 1989, 68-78.

Dean F. Sittig, Reed M. Gardner, Nathan L. Pace, Alan H. Morris, and Eduardo Beck, Computerized Management of Patient Care in a Complex, Controlled Clinical Trial in the Intensive Care Unit, Computer Methods and Programs in Biomedicine 30, 1989, 77-84.

Karen E. Bradshaw, Ph.D., Dean F. Sittig, Ph.D., Reed M. Gardner, Ph.D., T. Allan Pryor, Ph.D., and Marge Budd, R.N., M.S., Computer-Based Data Entry for Nurses in the ICU, Clinical Computing, Nov. 1988.

Robert A. Larsen, M.D., R. Scott Evans, Ph.D., John P. Burke, M.D., Stanley L. Pestonik, R.Ph., Reed M. Gardner, Ph.D., David C. Classen, M.D., Improved Perioperative Antibiotic Use and Reduced Surgical Wound Infections Through Use of Computer Decision Analysis, Computer Applications for Surgical Prophylaxis/Larsen et al.

R. M. Gardner, Computers in the ICU and Surgery-Keeping Real-Time Patient Records for Decision-Making.

Thomas D. East, Ph.D., Alan H. Morris, M.D., Terry Clemmer, M.D., James F. Orme, M.D., C. Jane Wallace, B.S.N., Susan Henderson, B.A., Dean F. Sittig, Ph.D., Reed M. Gardner, Ph.D., Development of Computerized Critical Care Protocols—A Strategy That Really Works!, 1990 LDS Hospital, Salt Lake City, UT.

R. Scott Evans, Ph.D., John P. Burke, M.D., Stanley L. Pestonik, R.Ph., David C. Classen, M.D., Ronald L. Menlove, Ph.D., and Reed M. Gardner, Ph.D., Prediction of Hospital Inflections and Selection of Antibiotics Using an Automated Hospital Database, 1990, SCAMC, Inc. 663-667.

Susan E. Henderson, B.A., Robert O. Crapo, M.D., Thomas D. East, Ph.D., Alan H. Morris, M.D., C. Jane Wallace, R.N., Reed M. Gardner, Ph.D., Computerized Clinical Protocols in an Intensive Care Unit: How Well are They Followed?, 1990, SCAMC, Inc., LDS Hospital, Salt Lake City, UT.

Reed M. Gardner, PHD, Russell K. Hulse, RPH, MBA, Keith G. Larsen, RPH, Assessing The Effectiveness Of A Computerized Pharmacy System, 1990, SCAMC, Inc., 668-672.

Reed M. Gardner, "Patient-Monitoring Systems", *Medical Informatics: Computer Applications in Health Care*, E.H. Shortliffe and L.E. Perrealt (eds.), G. Wiederhold and L.M. Fagan (assoc. eds.) (Reading, MA: Addison-Wesley, 1990.

Reed M. Gardner, Olaf K. Golubjatnikov, R. Myron Laub, Julie T. Jacobson, and R. Scott Evans, Computer-Critiqued Blood Ordering Using the HELP System, Computers and Biomedical Research 23, 514-528, 1990, Academic Press, Inc.

Karen E. Tate, PH.D., Reed M. Gard'ner, Ph.D., and Lindell K. Weaver, M.D., A Computerized Laboratoty Alerting System, Clinical Computing, 1990, vol. 7, No. 5, 296-301.

Dean F. Sittig, Reed M. Gardner, Alan H. Morris, and C. Jane Wallace, Clinical Evaluation of Computer-Based Respiratory Care Algorithms, International Journal of Clinical Monitoring and Computing 7, 1990, 177-185, Kluwer Academic Publishers, Netherlands.

R. Scott Evans, Stanley L. Pestotnilc, John P. Burke, Reed M. Gardner, Robert A. Larsen, and David C. Classen, Reducing Tile Duration Of Prophylactic Antibiotic Use Through Computer Monitoring Of Surgical Patients, DICP, The Annals of Pharmacotherapy, Apr. 1990, vol. 24, 351-354, Harvey Whitney Books Company, Cincinnati, OH.

Reed M. Gardner, and M. Michael Shabot, Computerized ICU Data Management: Pitfalls and Promises, International Journal of Clinical Monitoring and Computing 7: 99-105, 1990, Kluwer Academic Publishers, Netherlands.

Stanley L. Pestotnik, R.PH., R. Scott Evans, Ph.D., John P. Burke, M.D., Reed M. Gardner, Ph.D., David C. Classen, M.D., Therapeutic Antibiotic Monitoring: Surveillance Using a Computerized Expert System, The American Journal of Medicine, Jan. 1990, vol. 88, 43-48.

Gil Kuperman, MD, Brent James, MD, MSTAT, Julie Jacobsen, MT (ASCP), Reed M. Gardner, PHD, Continuous Quality Improvement Applied To Medical Care: Experiences At LDS Hospital, Medical Decision Making, Oct.-Dec. 1991, 60-65, vol. 11, No. 4.

Susan Henderson, Robert O. Crapo, C. Jane Wallace, Thomas D. East, Alan H. Morris, & Reed M. Gardner, Performance Of Computerized Protocols For The Management Of Arterial Oxygenation In An Intensive Care Unit, International Journal of Clinical Monitoring and Computing 8, 1992, 271-180, Kluwer Academic Publishers, Netherlands.

Reed M. Gardner, Ph.D., William L. Hawley, Thomas D. East, Ph.D., Thomas A. Oniki, B.S., Hsueh-Fen W. Young, B.S., Real Time Data Acquisition: Experience With the Medical Information Bus (MIB), LDS Hospital, University of Utah, Salt Lake City, UT.

Eric F. Lepage, MD, Reed M. Gardner, PhD, R. Myron Laub, MD, Julie T. Jacobson, MT(ASCP), Assessing The Effectiveness Of A Computerized Blood Order Consultation System, LDS Hospital, 1992, 33-37, AMIA, Inc.

R. Scott Evans, Ph.D., Stanley L. Pestotnik, R.PH., David C. Classen, M.D., Sheron B. Bass, B.S.N. Ronald L. Menlove, Ph.D., Reed M. Gardner, Ph.D., and John P. Burke, M.D., Development Of A Computerized Adverse Drug Event Monitor, LDS Hospital and University of Utah, Salt Lake City, UT.

E. Lepage, R. Traineau, PH. Marchetti, M. Benbunan, R. M. Gardner, Development Of A Computerized Knowledge Based System Integrated To A Medical Workstation: Application To Blood Transfusion, MEDINFO, 1992, 585-590, Elsevier Science Publishers B.V.

Reed M. Gardner, Ph.D. and R. Scott Evans, Ph.D., Computer-Assisted Quality Assurance, Group Practice Journal, May/Jun. 1992, 41(3), 8-11.

Thomas D. East, Ph.D., W. Hsueh-Fen Young, M.S., and Reed M. Gardner, Ph.D., Digital Electronic Communication between ICU Ventilators and Computers and Printers, Respiratory Care, Sep. 1992, vol. 37 No. 9, 1113-1123.

Reed M. Gardner, Computers in Critical Care, Wellcome Trends in Hospital Pharmacy, Jul. 1992.

T. Allan Pryor, Reed M. Gardner and W. Clinton Day, Computer System for Research and Clinical Application to Medicine, AFIPS—Conference Proceedings, vol. 33, 1968, 809-816.

Homer R. Warner, M.D., Reed M. Gardner and Alan F. Toronto, M.D., Computer-Based Monitoring of Cardiovascular Functions in Postoperative Patients, Supplement II to Circulation, Apr. 1968, vols. 37 & 38, 68-74.

Russell M. Nelson, Homer R. Warner, Reed E. Gardner and J. D. Mortensen, Computer Based Monitoring of Patients Following Cardiac Surgery, Computers in Cardiology, Jul.-Aug. 1969, vol. 5, No. 4, 926-930.

Reed M. Gardner, Computerized Patient Monitoring at LDS Hospital—An Evaluation, Proceedings of the San Diego Biomedical Symposium, 1971, vol. 10, 151-159.

Reed M. Gardner, Monitoring of Physiological Data in a Clinical Environment, Annual Review of Biophysics and Bioengineering, 1972, vol. 1, 211-224.

Reed M. Gardner, Computerized Intensive Care Monitoring at LDS Hospital—Progress and Development, 97-105.
Reed M. Gardner, Donald R. Bennet, and Richard B Vorce, Eight-Channel Data Set for Clinical EEG Transmission Over Dial-Up Telephone Network, IEEE Transactions on Biomedical Engineering, May 1974, vol. BME-21, No. 3, 246-249.
Reed M. Gardner, George H. Cannon, Alan H. Morris, Kenneth R. Olsen, W. Gary Price, Computerized Blood Gas Interpretation and Reporting System, Computer Magazine, Jan. 1975, 39-45.
Russell K. Hulse, Stephen J. Clark, J. Craig Jackson, Homer R. Warner and Reed M. Gardner, Computerized Medication Monitoring System, American Journal of Hospital Pharmacy 33, Oct. 1976, 1061-1064.
Reed M. Gardner, Ph.D., Computers in the ICU, Medical Electronics, Jun. 1984, 129-135.
Robert D. Andrews, M.S., M.T., Reed M. Gardner, Ph.D., Sandy M. Metcalf, R.R.T., and Deon Simmons, R.R.T., Computer Charting: An Evaluation of a Respiratory Care Computer System, Respiratory Care, Aug. 1985, vol. 30, No. 8, 695-707.
Reed M. Gardner, Ph.D., Computerized Data Management and Decision Making in Critical Care, Symposium on Critical Care, Aug. 1985, vol. 65, No. 4, 1041-1051.
Reed M. Gardner, David P. Scoville, Blair J. West, Beth Bateman, Robert M. Cundick, Jr., Terry P. Clemmer, Integrated Computer Systems for Monitoring of the Critically Ill, 1977, 301-307.
T. Allan Pryor, Reed M. Gardner, Paul D. Clayton, Homer R. Warner, A Distributed Processing System for Patient Management, Computers in Cardiology, Sep. 1978, 325-328.
Reed M. Gardner, Ph.D., Terry P. Clemmer, M.D., Keith G. Larsen, R.Ph., and Dickey S. Johnson, R.N., Computerized Alert System Use in Clinical Medicine, IEEE Session 6, 1979, 136-140.
T. Allan Pryor, Homer R. Warner, Reed M. Gardner, Help—A Total Hospital Information System.
T.P. Clemmer, R. M. Gardner, J. F. Orme, Jr., Computer Support in Critical Care Medicine, 1980.
Scott R. Cannon, and Reed M. Gardner, Experience with a Computerized Interactive Protocol System Using HELP, Computers and Biomedical Research 13, 1980, 399-409, Academic Press, Inc.
T. Allan Pryor, Paul D. Clayton, Reed M. Gardner, Randy Waki, and Homer R. Warner, HELP—A Hospital-Wide System for Computer-Based Support of Decision-Making, Jan. 1981.
T. A. Pryor, R. M. Gardner, P. D. Clayton and H. R. Warner, The HELP System, Proceedings of the Sixth Annual Symposium on Computer Applications in Medical Care, Oct.-Nov. 1982, 19-27, IEEE.
Reed M. Gardner, Information Management—Hemodynamic Monitoring, Seminars in Anesthesia, Dec. 1983, vol. 2, No. 4, 287-299.
T. A. Pryor, R. M. Gardner, P. D. Clayton, H. R. Warner, The HELP System, Journal of Medical Systems, 1983, vol. 7, No. 2, 87-102.
Reed M. Gardner, Blair J. West, T. Allan Pryor, Distributed Data Base and Network for ICU Monitoring, IEEE Computers in Cardiology, Sep. 18-24, 1984, 305-307.
Reed M. Gardner, T. Allan Pryor, Paul D. Clayton, And R. Scott Evans, Integrated Computer Network for Acute Patient Care, Symposium on Computer Applications in Medical Care, Nov. 4-7, 1984.
Reed M. Gardner, Tomorrow's Electronic Hospital is Here Today, IEEE Spectrum, Jun. 1984, 101-103.
Karen E. Bradshaw, Reed M. Gardner, Terry P. Clemmer, Jams F. Orme, Frank Thomas, and Blair J. West, Physician Decision Making—Evaluation of Data Used in a Computerized ICU, International Journal of Clinical Monitoring and Computing 1, 1984, 81-91.
Terry P. Clemmer, M.D., and Reed M. Gardner, Ph.D., Data Gathering, Analysis, and Display in Critical Care Medicine, Respiratory Care, Jul. 1985, vol. 30, No. 7, 586-601.
Reed M. Gardner, Ph.D., and William L. Hawley, Standardizing Communications and Networks in the ICU, Patient Monitoring and Data Management, 1985, 59-63.
R. Scott Evans, Reed M. Gardner, Allan R. Bush, John P. Burke, Jay A. Jacobson, Robert A. Larsen, Fred A. Meier, and Homer R. Warner, Development of a Computerized Infectious Disease Monitor (CIDM), Computers and Biomedical Research 18, 1985, 103-113.
Reed M. Gardner, Ph.D., Susan M. Monis, Paul Oehler, Monitoring Direct Blood Pressure: Algorithm Enhancements, 607-610.

R. Scott Evans, PhD, Robert A. Larsen, MD, John P. Burke, MD, Reed M. Gardner, PhD, Frederick A. Meier, MD, Jay A. Jacobson, MD, Marlyn T. Conti, BSN, Julie T. Jacobson, MT, Russell K. Hulse, RPH, Computer Surveillance of Hospital-Acquired Infections and Antibiotic Use, Journal of the American Medical Association, Aug. 22-29, 1986, vol. 256, No. 8, 1007-1011.
Reed M. Gardner, Computerized Management of Intensive Care Patients, Images, Signals, and Devices, 1986, vol. 3, No. 1.
R. Whiting, L. Hayes, The Practice of Telemedicine—The TARDIS Perspective, Informatics in Healthcare—Australia, Jul./Aug. 1997, vol. 6, No. 3, 103-106.
Monique Frize, Robin Walker, Clinical Decision-Support Systems for Intensive Care Units Using Case-Based Reasoning.
Ho Sung Lee, Seung Hun Park, and Eung Je Woo, Remote Patient Monitoring Service Through World-Wide Web, Proceedings—19th International Conference—IEEE/EMBS, Oct. 30-Nov. 2, 1997, 928-931.
Betty L. Grundy, M.D., Pauline Crawford, R.N., Paul K. Jones, Ph.D., May Lou Kiley, Ph.D., Arnold Reisman, Ph.D., Yoh-Han Pao, Ph.D., Edward L. Wilkerson, M.D., J. S. Gravenstein, M.D., Telemedicine in Critical Care: An Experiment in Health Care Delivery, Oct. 1977, 6:10.
Betty Lou Grundy, M.D., Paul K. Jones, Ph.D., and Ann Lovitt, M.D., Telemedicine in Critical Care: Problems in Design, Implementation, and Assessment, Critical Care Medicine, Jul. 1982, vol. 10, No. 7, 471-475.
Geraldine Fitzpatrick, TARDIS Evaluation: Report on Final Usage Evaluation of the TARDIS Telehealth System, Jul. 24, 1998, Issue No. 1.0.
Abstract Marie Delima, R.N., M. Michael Shabot, M.D., FACS, FCCM, FACMI, Karen Morris, R.N, Janet Mould, R.N., Eden Torre-Javier, R.N., Mark Lobue, B.A. and Jeannie Chen, Pharm.D., Successful Implementation of a Multiple-ICU Clinical Information System in a Tertiary Care Medical Center.
Xin Li, Daniel J. Valentino, George J. So, Robert Lufkin, Ricky K. Taira, A World Wide Web Telemedicine System, SPIE Vol. 2711, 427-439.
Stephen M. Ayres, M.D., F.C.C.M., Ake Grenvik, M.D., Ph.D., F.C. C.M., Peter R. Holbrook, M.D., F.C.C.M., william C. Shoemaker, M.D., F.C.C.M., Textbook of Critical Care, 3rd Edition, 1995, Harcourt Brace & Company.
Karen B. Tate, Ph.D., Reed M. Gardner, Ph.D., Kurt Scherting, Nurses, Pagers, and Patient-Specific Criteria; Three Keys to Improved Critical Valve Reporting, 1995, 164-168, AMIA, Inc.
Karen E. Tate, Ph.D., Reed M. Gardner, Ph.D., Computers, Quality, and the Clinical Laboratory: A Look at Critical Value Reporting, 17th Annual Symposium on Computer Applications in Medical Care, Oct. 30-Nov. 3, 1993, 193-197.
Peter J. Haug, Reed M. Gardner, Karen E. Tate, R. Scott Evans, Thomas D. East, Gilad Kuperman, T. Allan Pryor, Stanley M. Huff, and Homer R. Warner, Decision Support in Medicine: Examples from the HELP System, Computers and Biomedical Research 27, 1994, 396-418.
Thomas D. East, Ph.D., C. Jane Wallace, R.N., M.S., Alan H. Morris, M.D., Reed M. Gardner, Ph.D., and Dwayne R. Westenskow, Ph.D., Computers in Critical Care, New Technologies in Critical Care, Jun. 1995, vol. 7, No. 2, 203-216.
Reed M. Gardner, Ph.D., Bette B. Maack, R.R.A., R. Scott Evans, Ph.D., and Stanley M. Huff, M.D., Computerized Medical Care: The HELP System at LDS Hospital, Journal of AHIMA, Jun. 1992, 63(6):68-78.
Reed M. Gardner, Ph.D., Integrated Computerized Records Provide Improved Quality of Care with Little Loss of Privacy, Journal of the AMIA, Jul./Aug. 1994, vol. 1, No. 4, 320-322.
S Reddy, M Niewiadomska-Bugaj, Y V Reddy, H C Galfalvy, V Jagannathan, R Raman, K. Srinivas, R. Shank, T. Davis, S. Friedman, MD, B. Merkin, MD, M. Kilkenny,MD, Experience with ARTEMIS—An Internet-Based Telemedicine System, AMIA, 1997, 759-763.
Patrick R. Norris, M.S., Benoit M Dawant, Ph.D., Antoine Geissbuhler, M.D., Web-Based Data Integration and Annotation in the Intensive Care Unit, 1997.

H. C. Galfalvy, M.S., S. M. Reddy, Ph.D., M. Niewiadomska-Bugaj, Ph.D., S. Friedman, M.D., Evaluation of Community Care Network (CNN) System in a Rural Health Care Setting, 1995, AMIA Inc., 698-702.

K. Major, M. Shabot, S. Cunneen, Wireless Critical Alerts and Patient Outcomes in the Surgical Intensive Care Unit; The American Surgeon, 2000; p. 1057-1060.

M. Shabot, M. Lobue, Cedars-Sinai Medical Center Critical Alerting System, Feb. 2004; p. 1-16.

Shabot MM, LoBue M, Leyerle BJ, Dubin SB. Inferencing strategies for automated ALERTS on critically abnormal laboratory and blood gas data, SCAMC 1989; 13:54-57.

APACHE® III Equation Update (Version III-J) 2002, pp. 1-22.

APACHE® III Equation Update (Version III-I) 2003, pp. 1-13.

O. Kostopoulau, M. Wildman, Sources of Variability in Uncertain Medical Decisions In the ICU: A Process Tracing Study, Qual. Saf. Health Care 2004, 13:272-280.

A. Seiver, Critical Care Computing: Past, Present, and Future; Critical Care Clinics, vol. 16, No. 4, Oct. 2000, pp. 1-17.

J. Fisher, S. Harbarth, A. Agthe, A. Benn, S. Ringer, D. Goldmann, and S. Fancani, Quantifying Uncertainty: Physicians' Estimates of Infection in Critically Ill Neonates and Children; Clinical Infection Diseases 2004:38, pp. 1383-1390.

N. Halpern, S. Pastores, R. Greenstein, Critical Care Medicine in the United States 1985-2000: An Analysis of Bed Numbers, Use, and Cost; Critical Care Medicine 2004, vol. 32, No. 6, pp. 1254-1259.

J.Mrus, Getting Beyond Diagnostic Accuracy: Moving Toward Approaches That Can Be Used in Practice; Clinical Infectious Diseases 2004:38, pp. 1391-1393.

B. Leyerle, M. Shabot, Integrated Computerized Databases for Medical Data Management Beyond the Bedside, International Journal of Clinical Monitoring and Clinical Computing 1990:7, pp. 83-89.

M.Shabot, M. Lobue, B. Leyerle, S. Dubin, Decision Support Alerts For Clinical Laboratory and Blood Gas Data, Int. J. Clinical Monitoring and Computing 1990:7, pp. 27-31.

M. Shabot, M. Lobue, Real-Time Wireless Decision Support Alerts on a Palmtop PDA; Proc. Ann. Symp. Compt Appl. Med Care 1995, pp. 174-179.

G. Kuperman, D. Sittig, M. Shabot, J.Teich, Clinical Decision Support for Hospital and Critical Care, pp. 174-179.

W. Bates, M. Cohen, L. Leape, J. Overhage, M. Shabot, T. Sheridan, Reducing the Frequency of Errors In Medicine, J. American Medical Informatics Assn. 2001:8 pp. 299-308.

M. Shabot, B. Leyerle, M. Lobue, Automatic Extraction of Intensity Intervention Scores From A Computerized Surgical ICU Flowsheet, Am. J. Surg 1987:154:1, pp. 72-76.

Ho Sung Lee, Seung Hun Park, and Eunh Je Woo, Oct. 30-Nov. 2, 1997 Remote Patient Monitoring Service Through World Wide Web (17 pages).

Ho Sung Lee, Seung Hun Park, and Eunh Je Woo, "Remote Patient Monitoring Service Through World Wide Web", Oct. 30-Nov. 2, 1997.

Terry Ann Capuano, et al. "Remote Telemetry", Nursing Management, Jul. 1995, vol. 26, No. 7, p. 26.

Valeriy Nenov and John Klopp, "Remote Access to Neurosurgical ICU Physiological Data using the World Wide Web", Health Care in the Information Age, 1996, pp. 242-249.

Betty L. Grundy, et al., "Telemedicine in Critical Care: An Experiment in Health Care Delivery", JACEP, vol. 6, Oct. 1977, pp. 493-444.

Susan L. Mabry, et al., "Integrated Medical Analysis System", Proceedings of the 1997 winter Simulation Conference, 1997, pp. 1167-1168.

Simon M. Kaplan & Geraldine Fitzpatrick, "Designing Support for Remote Intensive-Care Telehealth Using the Locales Framework", ACM, 1997, pp. 173-184.

Douglas A. Peredina, "Telemedicine Technology and Clinical Applications", JAMA, Feb. 8, 1995, vol. 6.

Silvia Miksch, "Artificial Intelligence for Decision Support: Needs, Possibilities, and Limitations In the ICU", 10th Postgraduate Course in Critical Care Medicine, A.P.I.C.E. '95, Springer, 1995, pp. 1-11.

"Doctors use 'remote control' to monitor ICU patients", CNN.com, Aug. 21, 2000, http://www.cnn.com/2000/TECH/computing/08/21/icu.t_t/.

"Finding Value in Intensive Care, From Afar", The New York Times, Jul. 27, 1999, http://www.visicu.com/companynews/0799_nytimes.htm.

"Remote Monitoring of ICU Patients Lowers Mortality Rates, Complications", Johns Hopkins news release, Mar. 20, 2001, http://www.newswise.com/articles/2001/3/ICU.JHM.html.

Brian A. Rosenfeld, M.D., FCCM, FCCP, et al., "Intensive care unit telemedicine: Alternate paradigm for providing continuous Intensivist care", Critical Care Medicine, vol. 28, No. 12, 2000, p. 3925.

Benjamin Berg, Dale Vincent, and Donald Hudson, "Remote Critical Care Consultation: Telehealth Projection of Clinical Specialty Expertise", Tripler Army Medical Center, Honolulu.

Xin Li, et al., "A World Wide Web Telemedicine System", SPIE, vol. 2711, p. 427-439.

"Guidelines for Intensive Care Unit Design", Critical Care Medicine, Mar. 1995; 23(3):582-588.

Michael Breslow, et al., "Effect of a Multiple-Site ICU Telemedicine Program on Clinical and Economic Outcomes: An Alternative Paradigm for Intensivist Staffing", Critical Care Medicine, 2004, vol. 32, No. 1.

Richard Brilli, et al., "Critical Care Delivery in the ICU: Defining Clinical Roles and the Best Practice Model", Critical Care Medicine, 2001, vol. 29, No. 10.

M. Michael Shabot, et al., Decision Support Systems in Critical Care, 1994, Springer-Verlag Publishing, New York.

Definitions of Intensive Care Unit (ICU) on the Web, Apr. 2004, www.google.com and other websites.

Tsien, C.L. and Fackler, J.C., "Poor prognosis for existing monitors in the intensive care unit," Critical Care Medical Journal, vol. 25, No. 4 (1997) (p. 614-619).

Tsien, C.L. "Reducing False Alarms in the Intensive Care Unit: A Systematic Comparison of Four Algorithms," Proceedings Annual AMIA Fall Symposium (1997).

Kohane, I.S. and Haimowitz, I.J., "Hypothesis-Driven Data Abstraction with Trend Templates," Proceedings Annual AMIA Symposium on Computer Applications in Medical Care (1994), (p. 444-448).

Tsien, Christine L., "TrendFinder: Automated Detection of Alarmable Trends", Department of Electrical Engineering and Computer Science, Massachusetts Institute of Technology, Massachusetts; Jun. 2000.

Hosseinzadeh, Abolfazl, "A Rule-Based System for Vital Sign Monitoring in Intensive Care", Department of Electrical Engineering, McGill University, Montreal; Nov. 1993.

Aukburg, S.J. et al., "Automation of Physiological Data Presentation and Alarms in the Post Anesthesia Care Unit." In Symposium on Computer Applications in Medical Care, Nov. 5-8, 1989, Washington, DC; pp. 580-582.

Benis, A. M. et al., "Improved Detection of Adverse Cardiovascular Trends with the Use of a Two-Variable Computer Alarm" *Critical Care Medicine*, vol. 8, No. 2, Jun. 1980: 341-344.

Bierman, M. I. et al., "Pulse Oximetry in the Postoperative Care of Cardiac Surgical Patients; A Randomized Controlled Trial." *Chest*, vol. 102, No. 5, Nov. 1992: 1367-1370.

Bradshaw, K. E., "Computerized Alerting System Warns of Life-Threatening Events." In Symposium on Computer Application in Medical Care, Oct. 25-26, 1986, Washington, DC; pp. 403-409.

Chizeck, H. J., "Modeling, Simulation and Control in a Data Rich Environment." In Symposium on Computer Applications in Medical Care, Oct. 25-26, 1986, Washington, DC; pp. 65-69.

Coiera, E., "Intelligent Monitoring and Control of Dynamic Physiological Systems." *Artificial Intelligence in Medicine*, vol. 5, 1993: pp. 1-8.

Colvin, J. R. et al., "Microcomputer-Controlled Administration of Vasodilators Following Cardiac Surgery: Technical Considerations." *J. Cardiothoracic Anesthesia*, vol. 3, No. 1, Feb. 1989: pp. 10-15.

Coplin, W. M. et al., "Accuracy of Continuous Jugular Bulb Oximetry in the Intensive Care Unit." Neurosurgery, vol. 42, No. 3, Mar. 1998: 533-540.

Crew, A. D. et al., "Preliminary Clinical Trials of a Computer-Based Cardiac Arrest Alarm." Intensive Care Med, vol. 17, 1991: 359-364.

Garfinkel, D. et al., "PONI: An Intelligent Alarm System for Respiratory and Circulation Management in the Operating Rooms." In Symposium on Computer Applications in Medical Care, Nov. 6-9, 1988, Washington, DC; pp. 13-17.

Garfinkel D. et al., "Patient Monitoring in the Operating Room: Validation of Instrument Reading by Artificial Intelligence Methods." In Symposium on Computer Applications in Medical Care, Nov. 5-8, 1989, Washington, DC; pp. 575-579.

Guedes de Oliveira, P. et al., "The Role of Computer Based Techniques in Patient Monitoring: Technical Note." *Acta Neuorchir*, vol. 55, 1992 (Suppl.): 18-20.

Hahnel, J. et al., "Can a Clinician Predict the Technical Equipment a Patient will Need During Intensive Care Unit Treatment? An Approach to Standardize and Redesign the Intensive Care Unit Workstation." *J Clinical Monitoring*, vol. 8, No. 1, Jan. 1992: 1-6.

Hall, G. L. & P.B. Colditz, "Continuous Physiological Monitoring: An Integrated System for Use in Neonatal Intensive Care." *Australian Physical & Engineering Sciences in Medicine*, vol. 18, No. 3, 1995; 139-142.

Hayes-Roth, B. et al., "Guardian: An Experimental System for Intelligent ICU Monitoring." In Symposium on Computer Applications in Medical Care, Nov. 5-9, 1994, Washington, DC; p. 1004.

Irazuzta, Jose, "Monitoring in Pediatric Intensive Care." *Indian J. Pediatrics*, vol. 60, 1993: 55-65.

Jans, R. et al., "A Low Cost ECG Central Station for Intensive Care." *Australian Physical & Engineering Sciences in Medicine*, vol. 13, No. 1, 1990: 31-35.

Jastremski, M. et al., "A Model for Technology Assessment as Applied to Closed Loop Infusion Systems" *Critical Care Medicine*, vol. 23, No. 10, Oct. 1995: 1745-1755.

Klass, M. A. & E. Y. Cheng, "Early Response to Pulse Oximetry Alarms with Telemetry." *J. Clinical Monitoring*, vol. 10, No. 3, May 1994: 178-180.

Koski, E. M. J. et al., "A Knowledge-Based Alarm System for Monitoring Cardiac Operated Patients—Assessment of Clinical Performance." *International J Clinical Monitoring and Computing*, vol. 11, 1994: 79-83.

Koski, E. M. J. et al., "Development of an Expert System for Haemodynamic Monitoring: Computerized Symbolism of On-Line Monitoring Data." *International J. Clinical Monitoring and Computing*, vol. 8, 1992: 289-293.

Laffel, G. et al., "Using Control Charts to Analyze Serial Patient-Related Data." *Quality Management in Health Care*, vol. 3, No. 1, Fall 1994: 70-77.

L'Estrange, P. R. et al., "A Microcomputer System for Physiological Data Collection and Analysis." *Australian Dental Journal*, vol. 3 8, No. 5, Oct. 1993: 400-405.

M. de Beer, N. A. et al., "Clinical Evaluation of a Method for Automatic Detection and Removal of Artifacts in Auditory Evoked Potential Monitoring." *J Clinical Monitoring*, vol. 11, No. 6, Nov. 1995: 381-391.

Makivirta, A. et al., "The Median Filter as a Preprocessor for a Patient Monitor Limit Alarm System in Intensive Care." *Computer Methods and Programs in Biomedicine*, vol. 34, No. 2/3, Feb./Mar. 1991: 139-144.

Makivirta, A. & E. M. J. Koski, "Alarm-Inducing Variability in Cardiac Postoperative Data and the Effects of Prealarm Delay." Critical Care Medicine, vol. 8, No. 6, May 1994: 153-162.

Martin, J. F., "Closed-Loop Control of Arterial Pressure During Cardiac Surgery." *J. Clinical Monitoring*, vol. 8, No. 3, Jul. 1992: 252-253.

Meyer, C., "Visions of Tomorrow's ICU." *American J. Nursing*, Apr. 1993: 27-3 1.

Nenov, V. I. et al., "Computer Applications in the Intensive Care Unit." *Neurosurgery Clinics of North America*, vol. 5, No. 4, Oct. 1994: 811-827.

Nobel, J. J., "Physiologic Monitoring Systems, Acute Care." *Pediatric Emergency Care*, vol. 8, No. 4, Aug. 1992: 235-237.

Orr, J. A. & Westenskow, D. R., "A Breathing Circuit Alarm System Based on Neural Networks." *J. Clinical Monitoring*, vol. 10, No. 2, Mar. 1994: 101-109.

Pappert, D. et al., "Preliminary Evaluation of a New Continuous Intra-Arterial Blood Gas Monitoring Device." *Acta Anaesthesiologica Scandinavica*, Suppl. 107, vol. 39, 1995: 67-70.

Rampil, I. J., "Intelligent Detection of Artifact." *The Automated Anesthesia Record and Alarm Systems*, Chapter 17, 1987: 175-190.

Runciman, W. B. et al., "The Pulse Oximeter: Applications and Limitations—An Analysis of 2000 Incident Reports." *Anaesthesia and Intensive Care*, vol. 2 1, No. 5, Oct. 1993: 543-550.

Sailors, R. M., "A Model-Based Simulator for Testing Rule-Based Decision Support Systems for Mechanical Ventilation of ARDS Patients." In Symposium on Computer Applications in Medical Care, Nov. 5-9, 1994, Washington, DC; p. 1007.

Sanklecha, M., "The Pulse Oximeter." *Indian J. Pediatrics*, vol. 60, No. 3, 1993: 469-470.

Schnapp, L. M. & N. H. Cohen, "Pulse Oximetry; Uses and Abuses." *Chest*, vol. 98, No. 5, Nov. 1990: 1244-1250.

Simpson, R. L., "Automating the ICU: Facing the Realities." *Nursing Management*, vol. 23, No. 3, Mar. 1992: 24-26.

Sittig, D. F. & M. Factor, "Physiological Trend Detection and Artifact Rejection: A Parallel Implementation of a Multi-State Kalman Filtering Algorithm." In Symposium on Computer Applications in Medical Care, Nov. 5-8, 1989, Washington, DC; pp. 569-574.

Stoodley, K. D. C. et al., "Problems in the Development of a Computerized Ward Monitoring System for a Pediatric Intensive Care Unit." *International J Clinical Monitoring and Computing*, vol. 8, 1992: 281-287.

Sukavaara, T. et al., "A Knowledge-based Alarm System for Monitoring Cardiac Operated Patients—Technical Construction and Evaluation." *International J. Clinical Monitoring and Computing*, vol. 10, 1993: 117-126.

Szaflarski, N. L., "Emerging Technology in Critical Care: Continuous Intra-Arterial Blood Gas Monitoring." *American J. Critical Care*, vol. 5, No. 1, Jan. 1996: 55-65.

Uckun, S., ":Intelligent Systems in Patient Monitoring and Therapy Management." *International J. Clinical Monitoring and Computing*, vol. 11, 1994: 241-253.

Webb, R. K., "Medical Decision Making and Decision Analysis." *Anesthesia and Intensive Care*, vol. 16, No. 1, Feb. 1988: 107-109.

Yien, H. et al., "Spectral Analysis of Systemic Arterial Pressure and Heart Rate Signals as a Prognostic Tool for the Prediction of Patient Outcome in the Intensive Care Unit." *Critical Care Medicine*, vol. 25, No. 2, 1997: 258-266.

Tsien, Christine L. and James Fackler, "Poor Prognosis for Existing Monitors in the Intensive Care Unit" *Critical Care Medicine*, vol. 25, No. 4, 1997: 614-619.

Tsien, Christine L.. "Reducing False Alarms in the Intensive Care Unit: A systematic Comparison of Four Algorithms" Proceedings *AMIA* Symposium, 1997. pp. 9-14 (unnumbered).

Tsien, Christine L. "Reducing False Alarms in the Intensive Care Unit: A Systematic Comparison of Four Algorithms" Proceedings Annual *AMIA* Fall Symposium (1997), p. 8 94.

Tsien, Christine L. and James C. Fackler "An Annotated Data Collection System to Support Intelligent Analysis of Intensive Care Unit Data." Proceedings of the Second International Symposium on Advances in Intelligent Data Analysis, Reasoning about Data; Aug. 4-6, 1997; X. Liu, P. R. Cohen, and M. R. Berthold, Eds.; Springer-Verlag, London, UK; pp. 111-121.

Zhao, Ruilin, "A Model-Based Expert System for Interpretation of Hemodynamic Data from ICU Patients." Department of Electrical Engineering and Computer Science, Massachusetts Institute of Technology; May 18, 1997 (pp. 1-121).

Summary of iMDSoft, LTD's Counterclaims - Filed Dec. 10, 2007.

Response to Summary of iMDSoft, LTD's Counterclaims - Filed Dec. 28, 2007.

Clayton, Paul D.; Hripcsak, George. "Decision Support in Healthcare." *Intl. Journal of Bio-Medical Computing* 39 (1995), pp. 59-66.

Kuperman, Gilad J., et al. "Detecting Alerts, Notifying the Physician, and Offering Action Items: A Comprehensive Alerting System." Proceedings of the AMIA Annual Fall Symposium, 1996. Philadelphia: Hanley and Belfus, Inc. 1996; 20:704-708.

* cited by examiner

| Patient Description: | 45 y/o male with TAA presenting on 7/20/02 with atypical chest pain |
|---|---|
| HPI: | Presented to Sentara Beach with c/o atypical C/P. Dx with TAA, 12.5cm x 6.9 x 2.7, involving the renal arteries. Cardiac clearance for OR by nuclear stress scan - nl LV fx, small area of apical ischemia |
| Source of Pt Info: | medical records |
| Pre-Admission Meds: | xxccr, other, other, other, other |
| Allergies: | Penicillin |
| Past History: | CVASC-HTN, hypercholesterolemia; PULM-COPD, asthma; GI-hernia repair x 2 |
| Review of Systems: | CVASC-chest pain - atypical; PULM-denies COPD, denies bronchitis; ENDO-negative; MUSC-SKEL-negative |
| Social History: | Occupation-sales; married; ethanol use-rare; 20-40 pack years - still smoking; DRUG ABUSE-no |
| Family History: | CAD-father; cancer-sister; has polycystic disease |
| Physical Exam: | HR-62, sinus, with PACs; BP-120/80; Tmax-98.5; Resp-20, stridorous; O2 sat-92; FiO2-60; PEEP-10
CVP-12; PAOP-17; CO-4.5; SVR-1250
Healthy appearing; obese; not in acute distress
NEURO - GCS: M-6, V-5, E-4; mental status: sedated, agitated at times, oriented x 3
Head/Neck - pupils: equal, react to light; conjunctivae: no icterus; ear: normal; mouth/pharynx: edentulous, small palatal erosion; neck: normal mobility, no tenderness, no JVD
PULM - not intubated; clear to percussion; bibasilar rales
CVASC - PMI: normal; S-1 normal, S-2 normal, no S-3, no S-4; no murmurs; pulses: L carotid decreased
GI - within normal limits
EXTREM - perfusion: adequate |
| Test Results: | cbc - 9.2, Hct - 29, WBC - 13.9, Plts - 196, INR - 1.36, , PTT - 58
Na - 134, K - 3.5, Cl - 103, HCO3 - 24, BUN - 22, Glu - 220, Ca - 8.2, Cr - 1.5, Phos - 4.4, Mg - 1.8, Albumin - 03, Total Protein - 40, AST (SGOT) - 22, ALT (SGPT) - 12, LDH - 98, Total Bilirubin - 2.2
Digoxin - 1.8, Theophylline - 12
pH - 7.36, PCO2 - 52, PO2 - 119, HCO3 - 19, vented, FiO2 - 50%, PEEP 5 |
| Assessment and Plan: | |
| NEURO | Problems: encephalitis-viral (herpes) |
| CVASC | Problems: chest pain-atypical, aortic aneurysm, hypertension
Treatment: beta blocker, oxygen therapy (<40%)
TAA - for OR Monday, on SNP and Ipressor, needs beta blocker preop. Low risk coronary per nuclear scan. Active smoker w/ no known symptoms. Fu CXR, bronchodilators posted. Esop, DVT / GI prophylaxis / nutritional support |

| | |
|---|---|
| Neurologic: | Other - depression |
| Cardiovascular: | Congestive Heart Failure - Class I, Hypertension Requiring Treatment |
| Pulmonary: | Smoking Status - < 20 pack years - still smoking |
| Renal: | Renal Insufficiency - Creat 1 - 2 |
| Gastrointestinal: | Ethanol Use - Moderate (not daily) |
| Endocrine: | Non-Insulin Dependent Diabetes |

FIGURE 8

Web Page Dialog

Cardiovascular        Leg swelling;
Neurologic            Loss of consciousness;
Psychiatric           Depression;

SYSTEM AND METHOD FOR PHYSICIAN NOTE CREATION AND MANAGEMENT

CROSS REFERENCE TO OTHER PATENT APPLICATIONS

This application is a continuation-in-part of and claims priority to U.S. patent application Ser. No. 09/443,072, entitled "System And Method For Providing Continuous, Expert Network Critical Care Services From A Remote Location(s)" filed Nov. 18, 1999, now U.S. Pat. No. 6,804,656, which is hereby is incorporated by reference in this application in its entirety for all purposes.

BACKGROUND OF THE INVENTION

The present invention relates to a system and method for automating physician notes within an entire system of patient care and patient monitoring. For purposes of this application, the "patient care system" refers generally to the system in a hospital or other care facility that provides health care services to patient. Such a system comprises, without limitation, emergency rooms, operating rooms, laboratories, hospital rooms, data processing systems, monitoring equipment, administrative systems and billing systems.

While the severity of illness of ICU and other hospitalized patients over the past 15 years has increased dramatically, the level of and type of physician coverage has remained constant. Most hospitalized patients receive brief minutes of attention during morning rounds. During the remainder of the day and night, nurses are the primary caregivers, with specialists called only after patient conditions have started to deteriorate. One result of this mismatch between severity of illness and physician coverage is a high prevalence of avoidable errors that result in clinical complications. Exacerbating the problem is the inability of present days systems to incorporate and disseminate information derived from doctors and other hospital based physicians through the patient care system so that all observations and diagnoses are available to various hospital personnel in a timely way. In 1998, an Institute of Medicine Roundtable determined that avoidable patient complications were the single largest problem in medical care delivery. In another prominent 1998 study of 1000 patients, 46% experienced an avoidable adverse event in care, with 40% of these errors resulting in serious disability or death. Techniques that can limit these problems would be beneficial indeed, not only to patients but to the hospitals themselves.

The physicians who treat critically ill patients are in critically short supply. Numerous studies have shown that intensivists (physicians who have trained and board certified in Critical Care Medicine) can markedly improve patient outcomes. However, only one-third of all critically ill patients ever have an intensivist involved in their care, and the number of intensivists would need to increase seven-fold (nationally) to provide 24-hour coverage to all critically ill patients. With the rapid aging of the population, this shortfall of expertise is going to increase dramatically.

Even where intensivists are present (and especially where they are not), patients suffer from unnecessary variation in practice. There is little incentive for physicians to develop and conform to evidence-based best practices (it takes significant work and a change in behavior to develop and implement them). This variation contributes to sub-optimal outcomes, in both the quality and cost of care delivered to hospitalized patients.

What is needed, and is beginning to be fielded with great success, is a critical care regimen offered to critically ill patients. Such a system is described in Application for Letters patent Ser. No. 09/443,072, entitled "System And Method For Providing Continuous, Expert Network Critical Care Services From A Remote Location(S)" which is incorporated herein by reference. Rather than the traditional consultative model where a periodic visit takes place and the doctor then goes away, a more active 24-hour intensivist managed care is instituted via remote monitoring of geographically disparate healthcare locations. Such technology leverages the intensivists' expertise and standardizes the care afforded to critically ill patients. Further, continuous feedback to improve the practice of intensivists is necessary so that timely interventions can occur to minimize any adverse events. But even more can be done.

Attempts to automate various aspects of patient care have been the subject of various inventions. For example, U.S. Pat. No. 5,868,669 to Iliff was issued for "Computerized Medical Diagnostic and Treatment Advice System." The disclosed invention is for a system and method for providing computerized knowledge based medical diagnostic and treatment advice to the general public over a telephone network.

U.S. Pat. No. 5,823,948 to Ross, Jr. et al was issued for "Medical Records Documentation, Tracking and Order Entry System". The disclosed invention is for a system and method that computerizes medical records, documentation, tracking and order entries. A teleconferencing system is employed to allow patient and medical personnel to communicate with each other. A video system can be employed to videotape a patient's consent.

U.S. Pat. No. 4,878,175 to Norden-Paul et al. was issued for "Method for Generating Patient-Specific Flowsheets By Adding/Deleting Parameters." The disclosed invention is for an automated clinical records system for automated entry of bedside equipment results, such as an EKG monitor, respirator, etc. The system allows for information to be entered at the bedside using a terminal having input means and a video display.

U.S. Pat. No. 5,544,649 to David et al. was issued for "Ambulatory Patient Health Monitoring Techniques Utilizing Interactive Visual Communications." The disclosed invention is for an interactive visual system, which allows monitoring of patients at remote sites, such as the patient's home. Electronic equipment and sensors are used at the remote site to obtain data from the patient, which is sent to the monitoring site. The monitoring site can display and save the video, audio and patient's data.

U.S. Pat. No. 5,867,821 to Ballantyne et al. was issued for "Method and Apparatus for Electronically Accessing and Distributing Personal Health Care Information and Services in Hospitals and Homes." The disclosed invention is for an automated system and method for distribution and administration of medical services, entertainment services, and electronic health records for health care facilities.

U.S. Pat. No. 5,832,450 to Myers et al. was issued for "Electronic Medical Record Using Text Database." The disclosed invention is for an electronic medical record system, which stores data about patient encounters arising from a content generator in freeform text.

U.S. Pat. No. 5,812,983 to Kumagai was issued for "Computer Medical File and Chart System." The disclosed invention is for a system and method that integrates and displays medical data in which a computer program links a flow sheet of a medical record to medical charts.

U.S. Pat. No. 4,489,387 to Lamb et al. was issued for "Method and Apparatus for Coordinating Medical Procedures." The disclosed invention is for a method and apparatus that coordinates two or more medical teams to evaluate and treat a patient at the same time without repeating the same steps.

U.S. Pat. No. 4,731,725 to Suto et al. was issued for "Data Processing System which Suggests a Pattern of Medical Tests to Reduce the Number of Tests Necessary to Confirm or Deny a Diagnosis." The disclosed invention is for a data processing system that uses decision trees for diagnosing a patient's symptoms to confirm or deny the patient's ailment.

U.S. Pat. No. 5,255,187 to Sorensen was issued for "Computer Aided Medical Diagnostic Method and Apparatus." The disclosed invention is for an interactive computerized diagnostic system which relies on color codes which signify the presence or absence of the possibility of a disease based on the symptoms a physician provides the system.

U.S. Pat. No. 5,839,438 to Chen et al. was issued for "Intelligent Remote Visual Monitoring System for Home Health Care Service." The disclosed invention is for a computer-based remote visual monitoring system, which provides in-home patient health care from a remote location via ordinary telephone lines.

U.S. Pat. No. 5,842,978 to Levy was issued for "Supplemental Audio Visual Emergency Reviewing Apparatus and Method." The disclosed invention is for a system that videotapes a patient and superimposes the patient's vital statistics onto the videotape.

While these inventions provide useful records management and diagnostic tools, none of them provides a comprehensive method for inputting physician notes and populating patient care databases in real time regardless of where and when those physician notes are generated. In short, the inventions noted above are NOT designed for highly integrated hospital care.

What would be useful is a system and method for providing physician notes in a convenient manner, and integrating those notes throughput the patient care system whether it be for routine care or for care for the critically ill. Information from the physician notes (i.e. observations, thinking, and clinical plans for patients) would be immediately available to hospital personnel at all levels from administrative to those dealing directly with patients. Further, such information entered by a physician would be re-used to the maximum extent and in the most effective manner to provide information necessary for patient care and related administrative services.

BRIEF SUMMARY OF THE INVENTION

The present invention is a system and method for creation and dissemination of Physician notes.

It is an aspect of the present invention to integrate and coordinate diagnosis, diagnostic tests, treatment and monitoring actions and administrative functions with physician notes generated for any particular patient regardless of where the patient is in the healthcare system.

It is another aspect of the present invention to capture important clinical data for a patient one time and to re-use that information repeatedly throughout the patient care system.

It is yet another aspect of the present invention to automate recording of patient notes made in the course of patient care.

It is yet another aspect of the present invention to provide physicians with formatted options for creating detailed notes and diagnoses that facilitate use of the physician notes throughout the patient care system and associated databases.

It is a further aspect of the present invention to provide an automated system for communicating and coordinating the patient's medical history and treatment with a billing system.

It is a yet a further aspect of the present invention to provide an automated system for communicating the patient's updated medical information with medical treatment devices providing therapy to the patient.

It is yet another aspect of the present invention to help physicians detect patterns relating to temporal and contextual aspects of a patient that might otherwise go unnoticed.

It is still a further aspect of the present invention to provide customized patient diagnostic menus based upon the patients medical history and treatment plan and provide/report that information to hospital personnel at all levels in the patient care system as appropriate (i.e. not all hospital personnel require ALL information about a patient).

It is yet a further aspect of the present invention is an automated patient management system that records patient information and communicates the information to patient treatment stations to assist in administration of treatment and monitoring.

It is another aspect of the present invention to customize the pull down menu provided by the system to reflect a patient's medical history, diagnosis and treatment options.

It is yet another aspect of the present invention to automatically select and set patient alarm notifications and reminders to health care workers when a patient's medical treatment is due.

It is a further aspect of the present invention to provide risk assessment of specified therapies and notify the health care providers when therapies specified to the system are contraindicated.

It is yet another aspect of the present invention to respond to changing patient healthcare parameters by providing customized patient healthcare diagnostic and treatment menus specific for the changed state of the patient and to facilitate diagnosis.

It is yet a further aspect of the present invention to customize pick lists of patient care options to reflect the health care needs that are appropriate for each patient.

It is yet another aspect of the present invention to pre-load information for physician notes based upon prior notes so that further physician notes about a patient comprise information entered from prior notes thereby saving time in the note creation.

It is still another aspect of the present invention to link ICD-9 codes and CPT codes to the physician note entries to provide billing information to administrative parts of the patient care system.

These and other aspects of the present invention will become apparent to those skilled in the art from a review the general and specific descriptions that follow.

The present invention is a system and method for inputting physician notes associated with the admission, diagnosis and treatment of patients in a healthcare system. It can be used for those who are critically ill as well as those who are engaged in more routine medical care. The present invention reduces the risk of medical treatment by populating specific patient information throughout the patient care system so that current physician notes are combined with other information and made available rapidly to hospital personnel at all levels of patient care. The present invention also assists in analyzing data in relation to risk associated with management choices and managing the patient care to reduce assessed risk.

The system and method of the present invention can be implemented in a general purpose computer or a portable computer. It is equally suitable for use on Tablet PC's and personal digital assistants (PDA's) and for both wired and wireless systems.

The present invention provides physicians with a series of tools for creating detailed notes that document their findings and treatment plans. The note writing application of the present invention provides physicians with tools for creating detailed notes that document their findings and treatment plans. Through the use of physician notes and integration functions, clinical data is captured and re-used throughout the patient care system. By incorporating physician observations, assessments and plans into a patient care database, these data enable the intelligent systems that comprise the patient care system to provide more focused care and avoid errors that might otherwise occur. This, in turn, enhances the efficiency and effectiveness of patient care and resulting in superior clinical outcomes.

The note writing application of the present invention is available for use by any on-site physician. The present invention comprises templates for multiple different types of physician notes, including admission notes, brief and comprehensive progress notes, procedure notes and consultation notes. The note writing application uses a series of data-entry screens that break the notes into discrete sections. The bulk of the data are entered into the note using pre-defined selection options (e.g. pick list items, radio buttons, etc.). This both speeds note creation and captures discrete data elements, each of which relates to a specific patient at a specific point in time. The formatted nature of the data input by the physician are also easily accepted into the patient care database. All entries are time stamped by the present invention when they are released by the physician.

Over 1000 structured data elements are available for the physician note creation, covering admission data (demographics/admission date and time/admission diagnosis/past history/social history/family history/review of systems), physical examination findings, active diagnoses and treatments, and details of specific procedures). However, the number of entries is not meant as a limitation. It is anticipated that the number of formatted entry options will increase as knowledge of various treatments are added to the medical community generally. Free text fields are provided to allow entry of information not captured in the pick list options and for narrative detail, where needed. Conventional means such as keyboards, handwriting recognition, and voice recognition can be used for free text entry.

The end product of the note writing application of the present invention is a file that presents the selected options and free text entries in a format resembling a traditional physician's note. This file is stored electronically, after being signed electronically by the physician, for subsequent review within patient care system and can be configured to print a copy of the file for inclusion in the medical record or to export a file to hospital information systems. The note writing application is designed to provide substantially all required physician documentation options that a physician might normally need for creation of a patient record. The present invention can also be upgraded to add more options to the various note writing screens as more knowledge is gathered about patient care.

BRIEF DESCRIPTION OF THE DRAWINGS

FIG. 2 a screen of a completed admission note.

Figure 3:
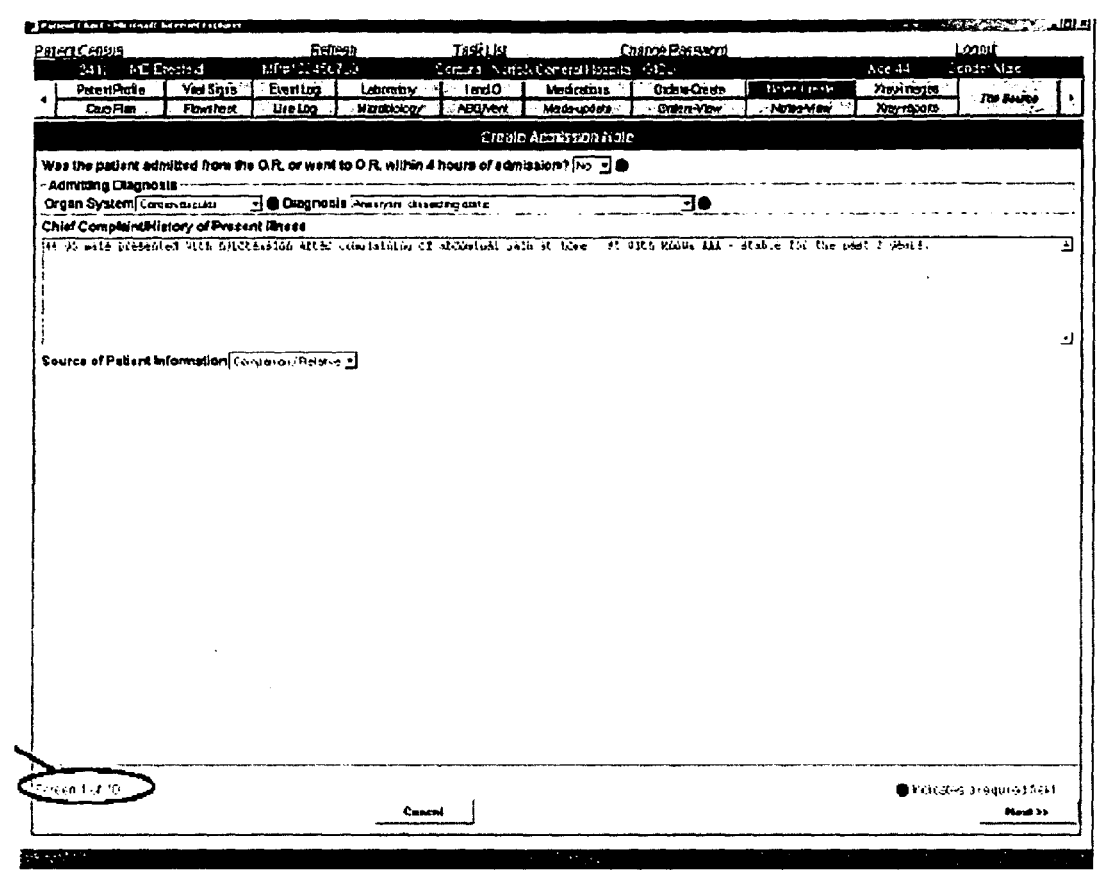

FIG. 3 illustrates an admitting diagnosis screen.

FIG. 4 illustrates surgical diagnosis screen.

FIG. 7 illustrates a screen of patient history summary.

FIG. 8 illustrates review of systems screen.

FIG. 12 illustrates today's diagnoses/today's diagnostics screen.

FIG. 14 illustrates billing information screen.

FIG. 15 illustrates final admission note screen.

Figure 16:
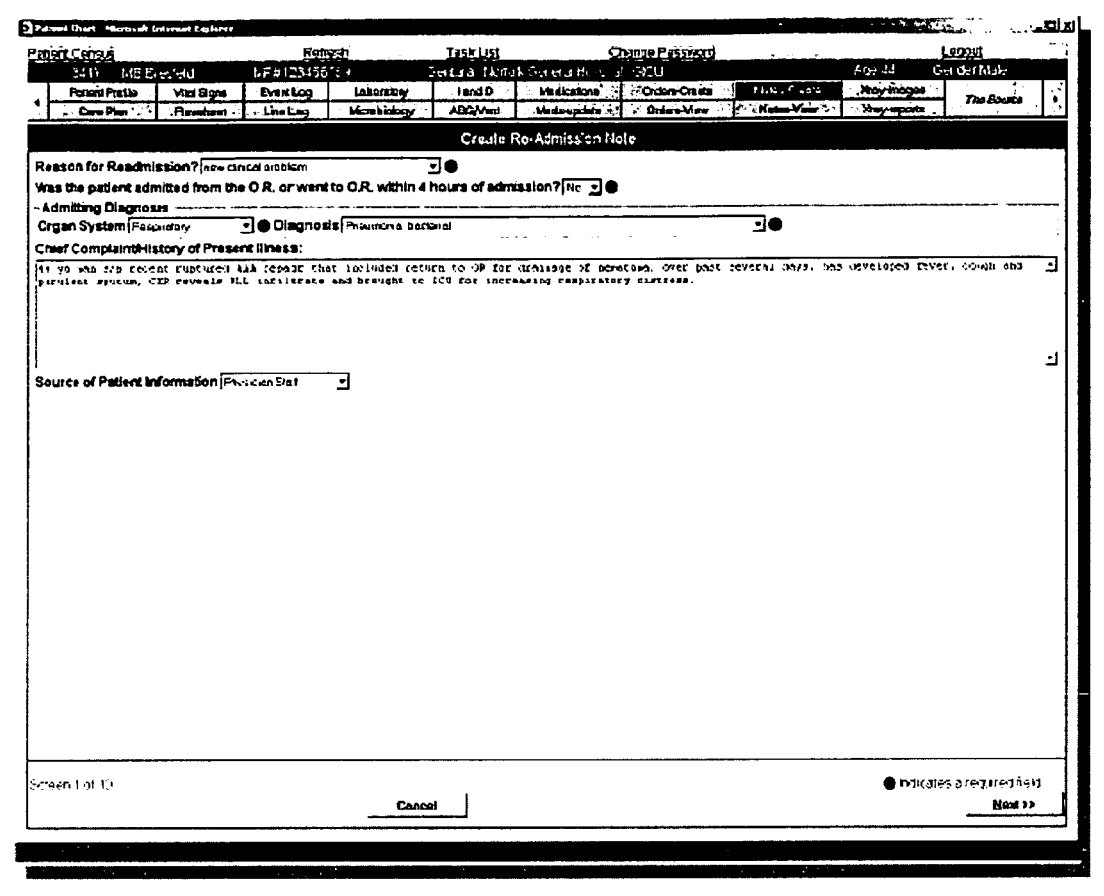

FIG. 16 illustrates a screen for a readmission note.

FIG. 17 illustrates a screen for surgical diagnosis.

FIG. 19 illustrates comprehensive progress note screen.

FIG. 22 illustrates a procedure note specifics screen

FIG. 23 illustrates a procedure note final screen.

FIG. 24 illustrates a notes view screen.

DETAILED DESCRIPTION OF THE INVENTION

As noted above the present invention is a system and method for providing a physician note writing functionality that is integrated into a patient care system. The present invention provides the physician with a wide variety of formatted patient related input options normally used by the physician in admission, diagnosis, physical finding and other factors. Once released by the physician, the patient notes are populated throughout the patient care system to aid in patient care, set alarms for patient physiological data, and to monitor best practices to name but a few functions. Physician notes, and the data contained therein, are also re-used and released (as appropriate) to administrative functions of the patient care system such a billing (ICD-9 and CPT codes), insurance form completion, Medicare and Medicaid aid requests and the like.

Figure 1:
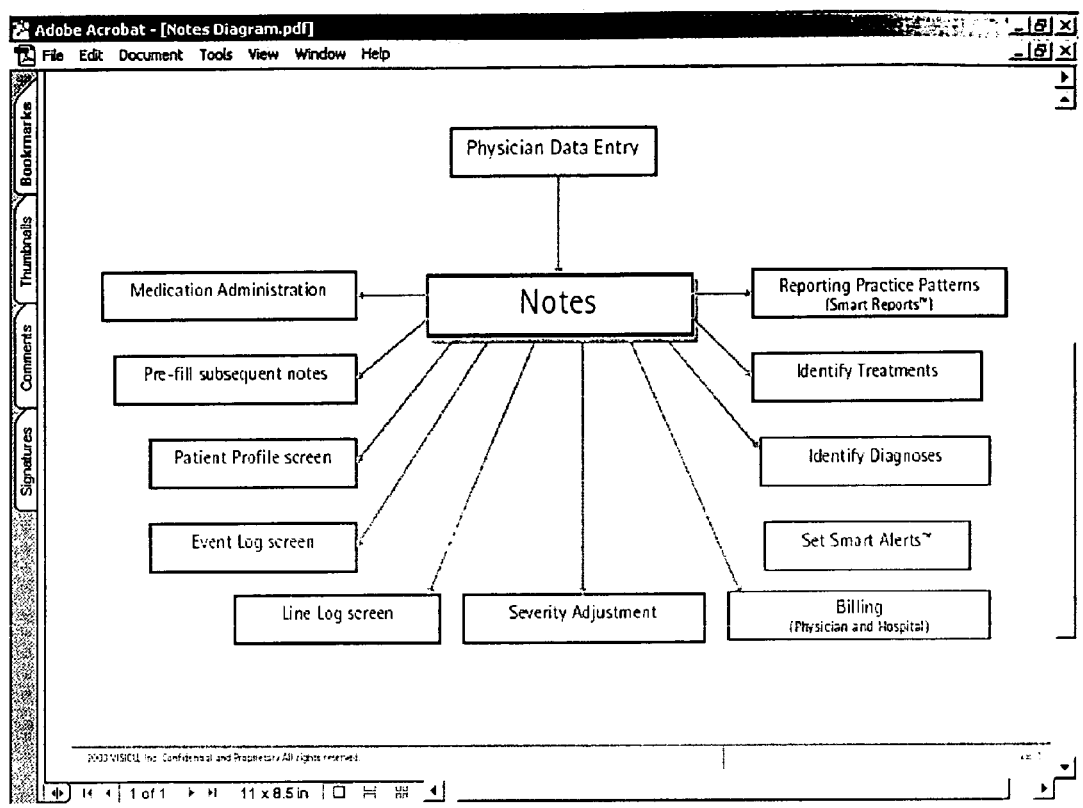
FIG. 1 illustrates a block diagram of functional areas receiving data from patient notes according to an embodiment of the present invention.

FIG. 1A illustrates a block diagram of functional areas receiving data from patient notes according to an embodiment of the present invention. The physician data entry produces a body of data referred to in FIG. 1A as "Notes." A subset of notes data is available to populate other administrative functions relating to the patient's care and the administration of the paperwork associated with that care. As illustrated in FIG. 1A, these functions comprise:

Medication Administration. Data fields as to allergies, preadmission medications, and prescribe medications are populated.

Pre-fill subsequent notes. Data fields regarding the patient that have been previously completed are pre-filled automatically in subsequent notes.

Patient Profile Screen. Note data are added to the patient profile information (e.g., active diagnoses and treatments).

Event Log screen. Basic patient data is added to the event screen.

Line Log screen. Note data are used to create/maintain the line log from physician procedure notes.

Severity Adjustment. Note data are used to populate severity adjustment tools (e.g., APACHE™ II or III scoring). The severity adjustment score is returned to the patient profile.

Billing (physician and hospital). Note data comprise all of information necessary to determine the charges for a patient.

Set Alerts (e.g., Smart Alerts™). Physician-entered data (active diagnoses and past history) automatically configures "smart" diagnostic systems to thresholds relevant to a particular patient allowing automatic monitoring of both absolute value and trends in those variables.

Identify Diagnoses. A diagnosis pick list is displayed in response to note data.

Identify Treatments. Customized patient healthcare diagnostic and treatment menus are displayed in response to note data.

Reporting Practice Patterns (e.g., Smart Reports™). Reports are created from the notes data. These reports profile how care is delivered—providing information not normally available to hospital administrators or physicians.

Following are more detailed descriptions of the options and actions presented to the physician by the present invention:

In accordance with a first aspect of the present invention, as embodied and broadly described herein, FIG. 1B illustrates completed admission note data. "Notes" are an important function of the integrated system of data management. In one embodiment of the present invention, a physician enters information about a patient as Notes. As illustrated in FIG. 1B, the Notes-Create button enables a physician to create physician notes that are recorded in a database of the patient care system. Data entered into Notes are used to populate other areas of the patient care system, such as the patient profile.

Five types of Notes are illustrated in this FIG. 1B. However, this is not meant as a limitation. Other types of notes are easily added as healthcare knowledge increases:

1. Admission Notes Admission Notes are required for each patient upon initial admission to the hospital or ICU. The system does not allow entry of a Comprehensive Progress Note until the Admission Note has been completed. One Admission Note is entered per initial visit to the hospital or ICU.
2. Readmission Notes are required for each readmission to the hospital or ICU. The system does not allow entry of a Comprehensive progress Note until the Readmission Note has been completed. One Readmission Note is entered per readmission to the hospital or ICU.
3. Comprehensive Progress Notes provide the physician with a means of tracking and documenting a patient's progress.
4. Brief Progress Notes Provides the physician a means of documenting events in a patient's progress.
5. Procedure Notes provide the physician a means of tracking and documenting procedures that were performed on a patient.

There are two types of Admission Notes: Medical and Surgical. The procedures for admission in each setting are different. In another aspect of the present invention, a surgical admission note is used for a patient that was admitted or came from the operating room (O.R.) in the past several hours. An Admission Note can be cancelled from any of the screens in the Create Note process by clicking the Cancel button. Options are provided to the user for closing the note or selecting the "Yes" button to go back to the Types of Notes screen. Selecting the "No" button returns the user to the current Admission Note.

An embodiment of the present invention is creating an admission note for a patient who was not admitted to the operating room before admission: selecting the Notes-Create button from the Patient Profile screen provides data fields for entering data as to the admitting Diagnosis. When a patient is admitted to the hospital or ICU as a medical patient, the user completes the Admitting Diagnosis fields by using the pick lists. Data is entered as to complete the Chief Complaint/History of Present Illness data fields. Data is entered as to the Source of Patient Information from a pick list.

Yet another aspect of the present invention is creating an Admission Note for a surgical patient. To create an Admission Note for a patient who was admitted to the hospital or ICU from the operating room, a user selects the Admission link. Data is entered in the required surgery fields as to the Surgical Diagnosis, the organ system involved (selected from the pick lists), the required elective surgery, and the Surgical Diagnosis fields selected from the pick lists. The Diagnosis pick list is displayed in response to the admission note populating the surgery fields. Data is entered to complete the Post-Operative Status information. Data as to the Chief Complaint/History of Present Illness is entered from the Source of Patient Information pick list.

Data fields as to Allergies and Pre-Admission Medications are populated from the Allergies and Pre-Admissions Medications pick lists. The Allergies and Pre-Admission Medications menu displays the Select Drug(s) screen. The present invention also checks for drug allergies and contraindications for any drug and conveys to the physician any such drug allergy or other indications that may be stored concerning the patient.

Figure 4:
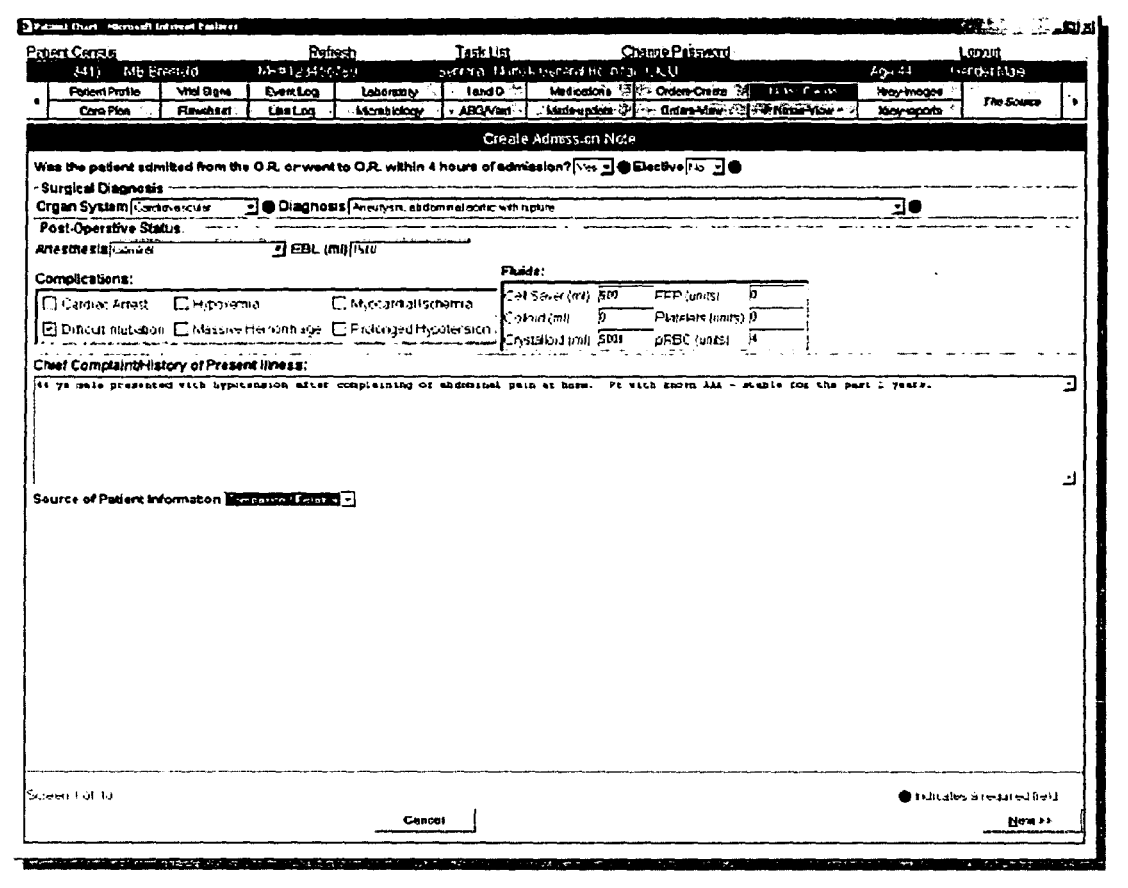

FIG. 4 illustrates data fields populated as to allergies and pre-Admission medications. In one embodiment data are entered from the Allergies and Pre-Admissions Medications pick lists when applicable. Data as to drugs prescribed to the patient and drugs taken by the patient are entered from a Select Drug(s) screen.

Figure 5:
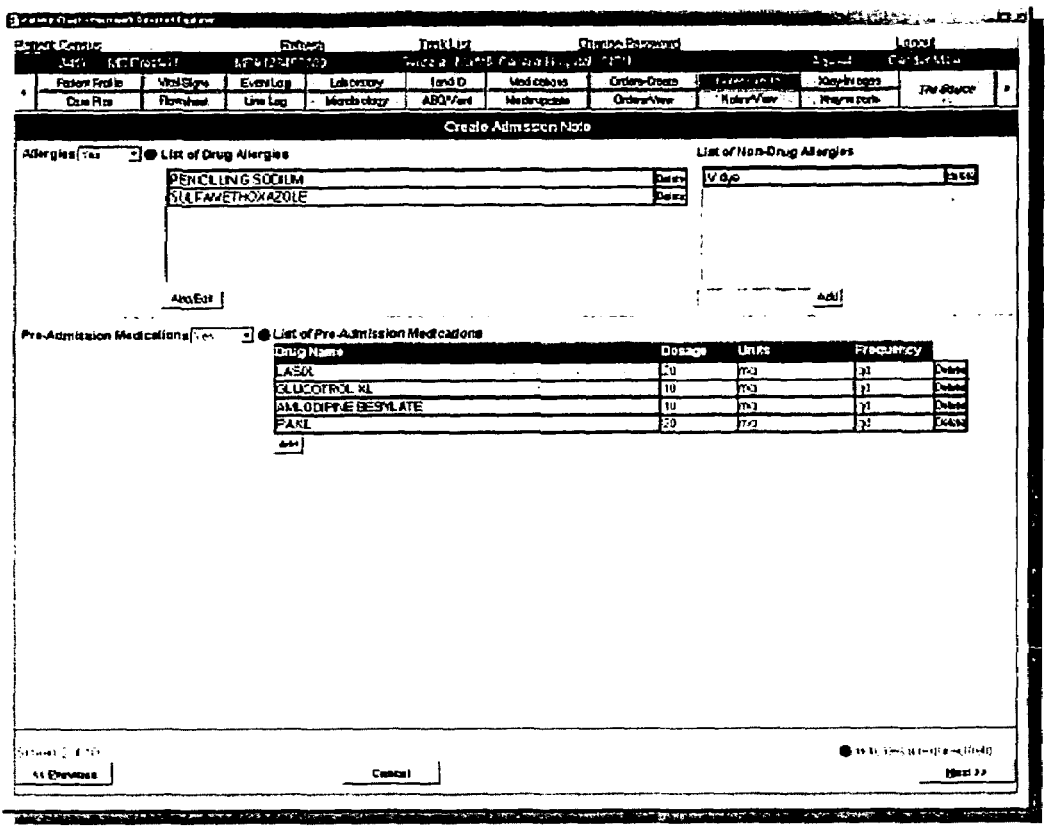
FIG. 5 illustrates allergies and preadmission medications screen.
Figure 6:
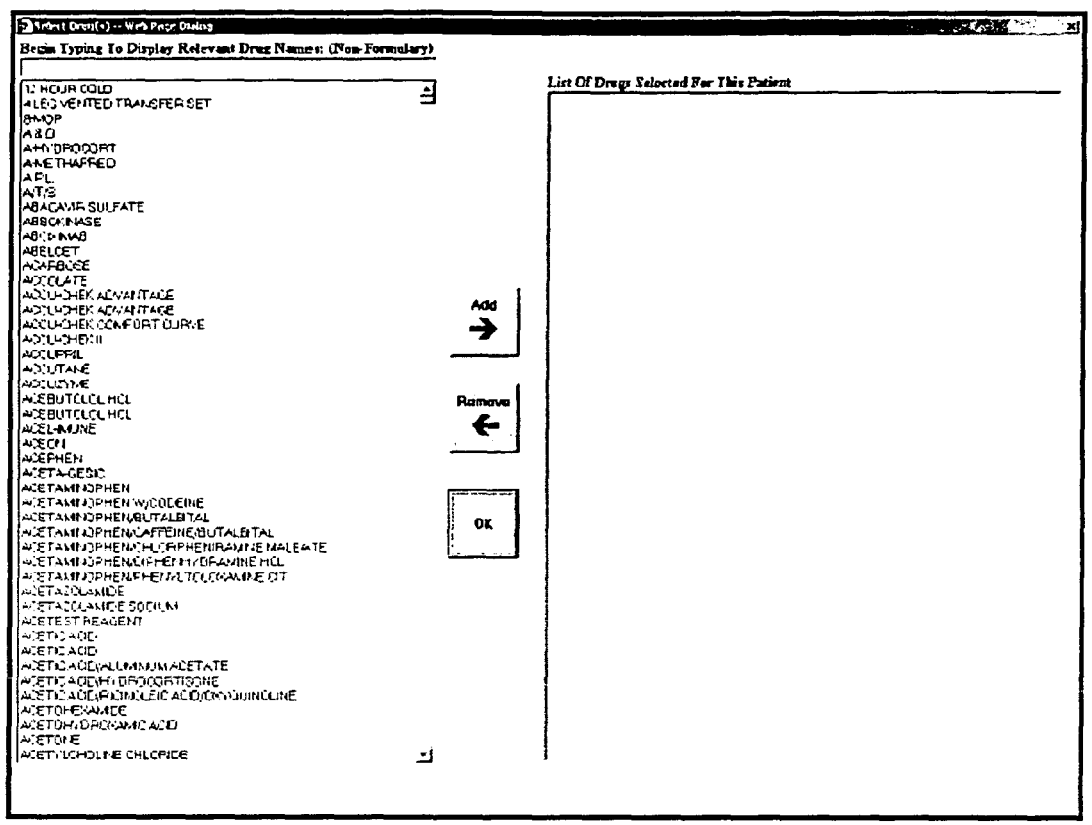
FIG. 6 illustrates select drug(s) screen.

FIG. 5 illustrates one aspect of a Select Drugs(s) screen. Once the relevant drug is selected, the name of the drug can be typed in or selected form a list. The selected drug is added to the List of Drugs Selected for this Patient on the right side of the screen. Multiple drugs can be added by repeating the selection process until all the appropriate drugs are added. Data as to a non-drug allergy may also be entered. Data as to Pre-Admission Medications is entered in the Select Drugs field. As illustrated in FIG. 5, the relevant drug from the left side of the screen may be added or removed from the patient list. The name of the drug or use the mouse to scroll and select the name of the drug. Dosage, units and frequency for preadmission medications are entered in the medication field.

A patient's Past History is also viewable in the present invention. The Past History information fields are displayed for population by data entry for procedures Performed and Not Performed, where information is or where information is not obtainable or where no health problems exist. Data entered as performed permits the user to enter past history information and access the past history menu. This is the default setting. Once data as to the Past History is entered, the user enters data as to at least one Past History field. All Past History fields are optional and should be completed as appropriate for each patient.

Data entry for past history fields is optional. If data is entered, the user enters information as to the status of Neurologic, Cardiovascular, Pulmonary, Renal, gastrointestinal, Infectious Disease, Hematology/Oncology, Endocrine, Rheumatic, systems. Data entries will generate custom pick lists with additional fields to complete for data entry.

For example, selecting Yes for TIA(s) causes the system to display a pick list titled "multiple" to allow you to indicate multiple TIA(s). As Past History information is added, you can show and/or refresh the Past History Summary, which displays a separate window showing the Past History as it will appear in the final printed Note.

To enter a patient's Past History information: A user selects the desired section button (e.g. 1-Neurologic) in the Past History menu or uses the scroll feature on the right side of the screen.

FIG. 7 illustrates the Patient History Summary displayed as the Patient History Summary in a separate window. This summary displays for the physician summaries of various conditions of the patient such as past medical conditions and individual habits such as smoking.

Figure 8:
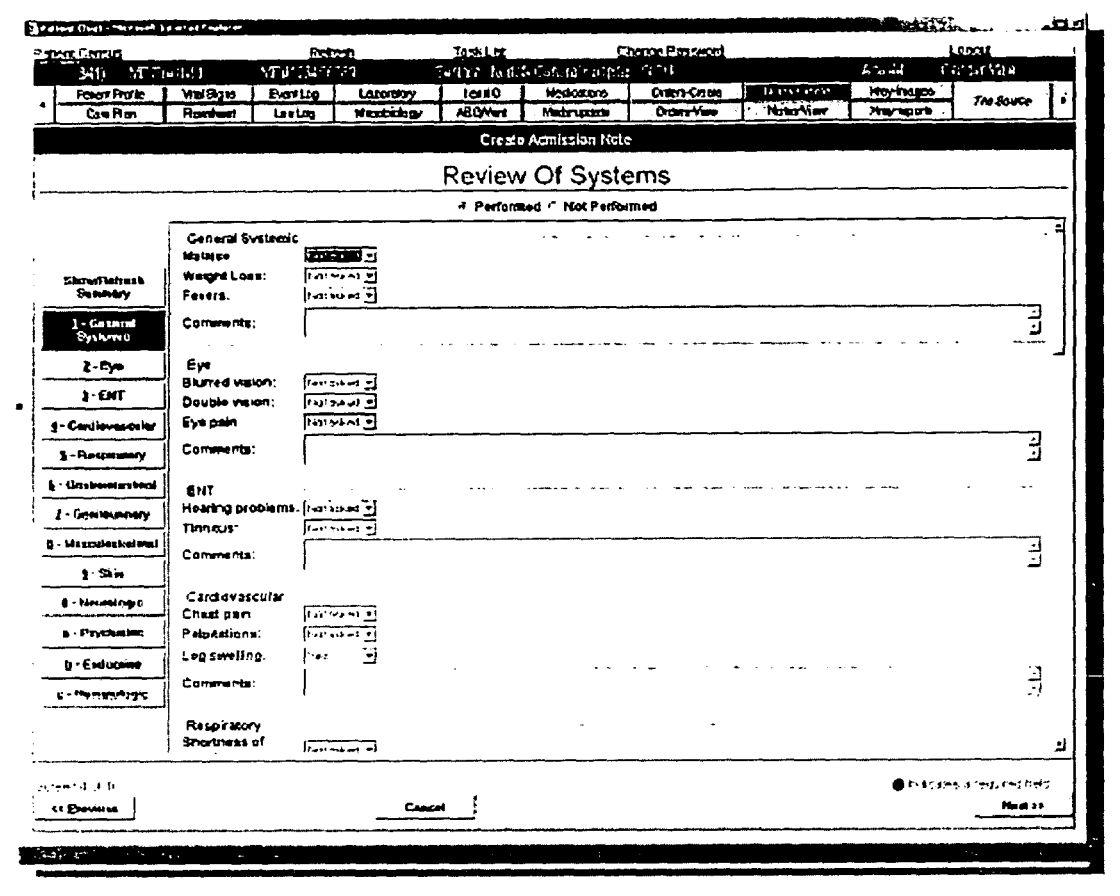

FIG. 8 illustrates aspects of the review of systems fields to be populated. A user in the Review of Systems field selects either Performed or Not Performed. A user navigates the Review of Systems fields by selecting the appropriate menu buttons on the left side of the screen. As each menu button is selected, the information fields displayed on the right change so that only those fields that are associated with each menu appear. Highlighting a selection will notify the user as to which selection is being considered. Selecting the Performed button permits you to enter Review of Systems information and access the Review of Systems menu. If Review of Systems is performed, the system requires completion of at least one "Review of Systems" field. The "Review of Systems" information fields are: General Systemic, Eye, ENT, Cardiovascular, Respiratory, Gastrointestinal, Musculoskeletal, Skin, Neurologic, Psychiatric, Endocrine, Hematologic. Throughout Review of Systems, certain pick list selections will cause additional fields and/or pick lists to appear as necessary to complete data entry. As Review of Systems data is added, a physician can show and/or refresh the Review of Systems Summary, which displays a separate window showing the Review of Systems as it will appear in the final printed Note. All or some of the Review of Systems information can be entered.

Figures 9, 10:
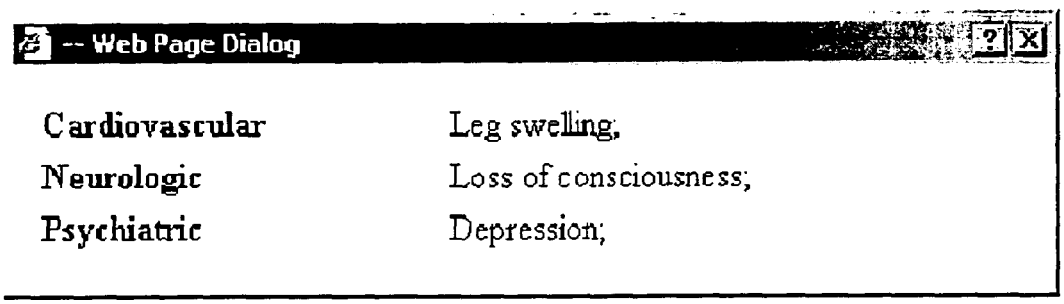
FIG. 9 illustrates review of systems summary.
FIG. 10 illustrates social history/family history screen.

An exemplary approach to patient management utilizing the one embodiment is the following: Select General System in the Review of Systems menu. Select the necessary information from the pick lists. After all necessary Review of Systems information has been entered; the Review of Systems Summary is refreshed. This displays the Review of Systems Summary. FIG. 9 illustrates the Review of Systems Summary screen.

The Social History and Family History display has two options 1. Performed and 2. Not Performed. The Performed option is the one option that permits a physician to enter Social History information and access the Social History pick lists. The performed option is the default setting. This is also true for Family History. Throughout Social History, certain pick list selections will cause additional fields and/or pick lists to appear as necessary to complete data entry. Selecting Not Performed removes all Social History information on the screen. This is also true for Family History. In Social History, the patient's marital status is derived from ADT information. The patient's smoking status, ethanol use and IV drug abuse information are derived from the patient's Past History information. Any changes in Social History information are reflected in Past History. Data as to the patient's Social History information is selected from information from the pick lists. FIG. 10: illustrates data entry fields where Social History/Family History screen information can be entered.

Figure 11:
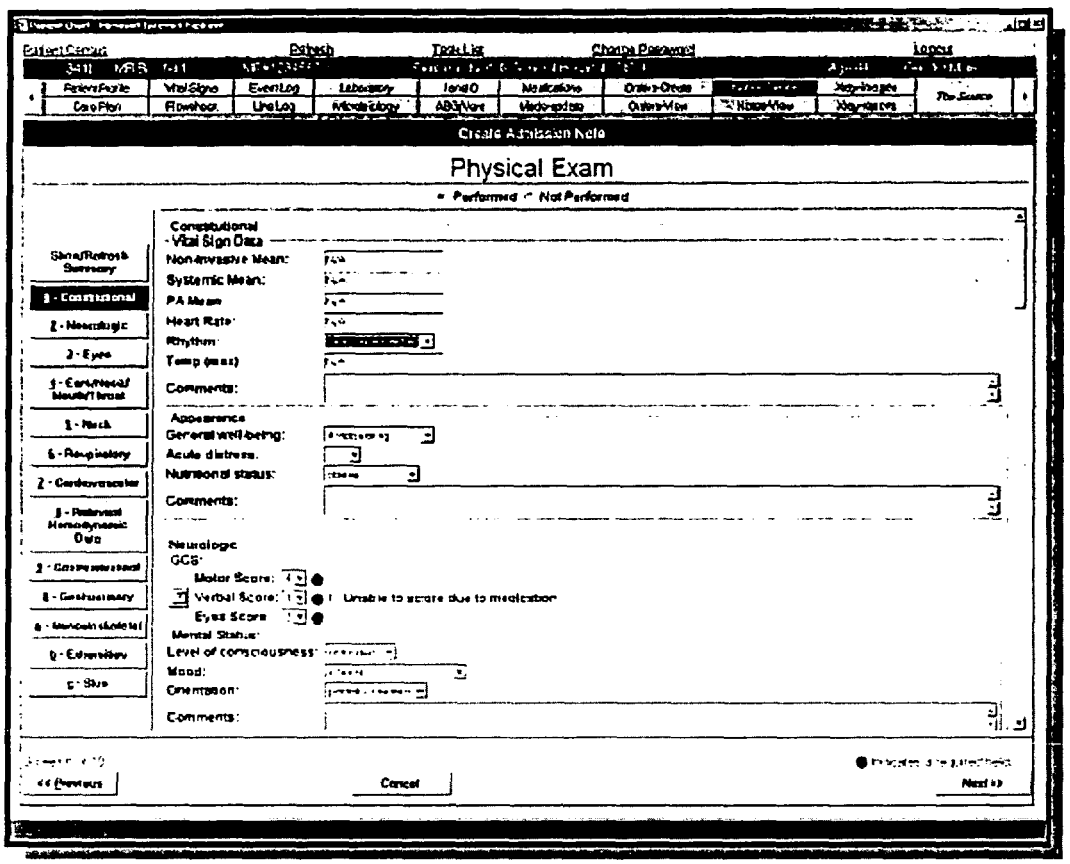
FIG. 11 illustrates physical exam screen.

The Physical Exam data fields have two options: 1. Performed and 2. Not Performed. The Performed option is the only option that permits you to enter Physical Exam information and access the Physical Exam pick lists. Selecting Not Performed removes all the Physical Exam information on the screen and the menu on the left side of the screen. The Physical Exam data fields available for population are Constitutional, Neurologic, Eyes, Ears/Nose/mouth/Throat, Neck, Respiratory, Cardiovascular, Relevant hemodynamic Data, Gastrointestinal, Genitourinary, Musculoskeletal, Extremities, and Skin FIG. 11 illustrates physical exam data fields. Data comes into some of the data fields based upon the bedside monitors for the particular patient. Data is also entered into the Physical Exam fields by selecting the appropriate options on the left side of the screen. As each menu button is selected, the information fields displayed on the right change so that only those fields that are associated with each menu appear and are highlighted in yellow. Throughout Physical Exam, specific pick list selections cause additional fields and/or pick lists to appear as necessary to complete data entry As Physical Exam information is added, a user can show and/or refresh the Physical Exam Summary. The following pertinent data are listed in the Physical Exam data fields: Constitutional, Non-Invasive, Mean, Defaulted, from most recent 10-minute median, near non-invasive arterial blood pressure value in Vital Signs, Systemic Mean Defaulted from most recent 10-minute median, near PA blood pressure value in Vital Signs, PA Mean Defaulted from most recent 10-minute median in Vital Signs, Heart Rate Defaulted from most recent 10-minute median in Vital Signs Temp Defaulted from Temp Max entry in I & O. Neurologic GCS Required for Admission Notes and Readmission Notes. Click "?" to view details of the score 13 Respiratory Oxygenation—SAO2 Defaulted from most recent 10 minute median SaO2 in Vital Signs Relevant hemodynamic Data, CVP Defaulted from most recent 10 minute median CMP value in Vital Signs, PAOP Defaulted from most recent pulmonary artery occlusion pressure value in Vital Signs, CO Defaulted from most recent 10 minute cardiac output median in Vital Signs, SVR Defaulted from most recent systemic vascular value in Vital Signs. The above listed values, if available, will default along with the date and time of the data. All defaulted values must be validated by the physician and can be edited or removed to ensure accurate entry in the printed Note. When the patient's Physical Exam information is entered, the Next button is clicked. To complete the patient's Physical Exam information the physician selects the desired section (e.g. 1-General Systemic) in the Physical Exam menu. Select the necessary information from the pick lists.

FIG. 11 illustrates data fields to be populated with information regarding Today's Problems/Diagnoses, and Today's treatments/Diagnostics. Today's problems/diagnoses is on the left side of the screen, and Today's treatments/diagnostics is on the right side of the screen. To complete Today's problems/diagnoses, Today's treatments/diagnostics: a user selects the Organ System involved. A list of problems associated with the selected system appears on the bottom of the screen. Selecting a link displays additional information associated with that system. After an item from the list. Is selected, a check next to the selected information, which will be displayed in Today's problems/Diagnosis section of the screen.

Figure 12:
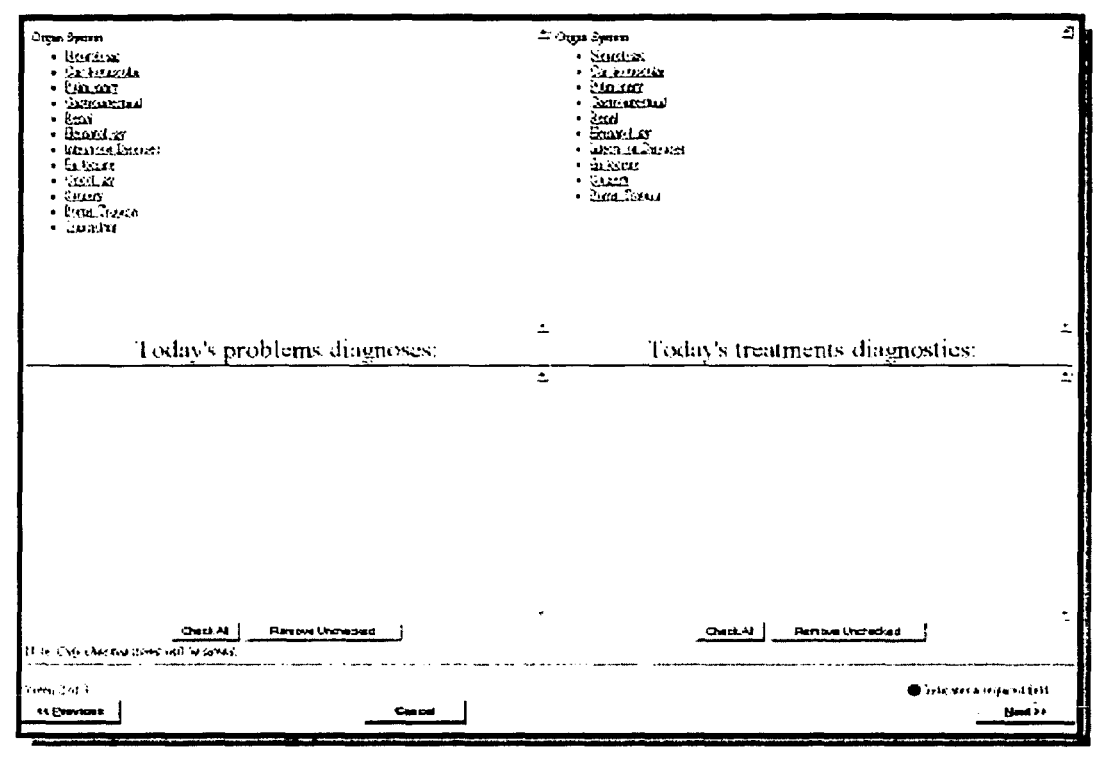

FIG. 12 illustrates, Today's diagnoses/today's diagnostics screen. Laboratory Results to Print/Assessment and Plan, Table I lists all Lab Results for review. Data is entered and the data populates the fields of the patient care system in general.

Figure 13:
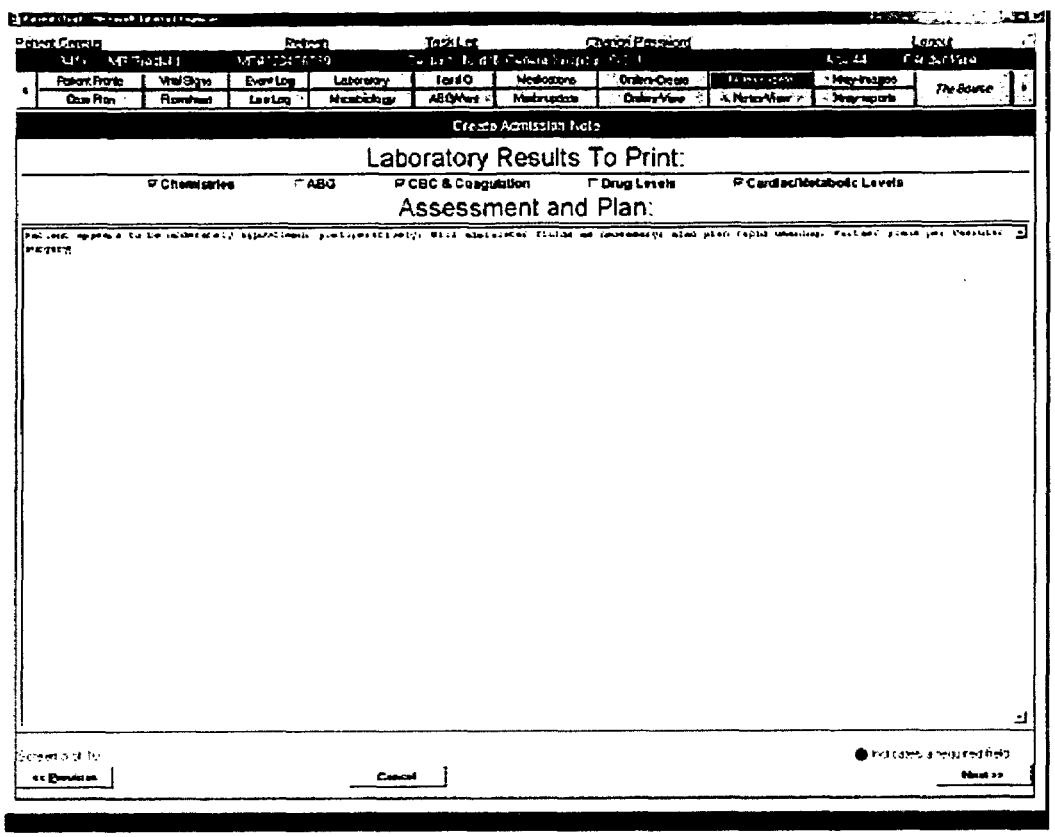
FIG. 13 illustrates laboratory results.
Figure 18:
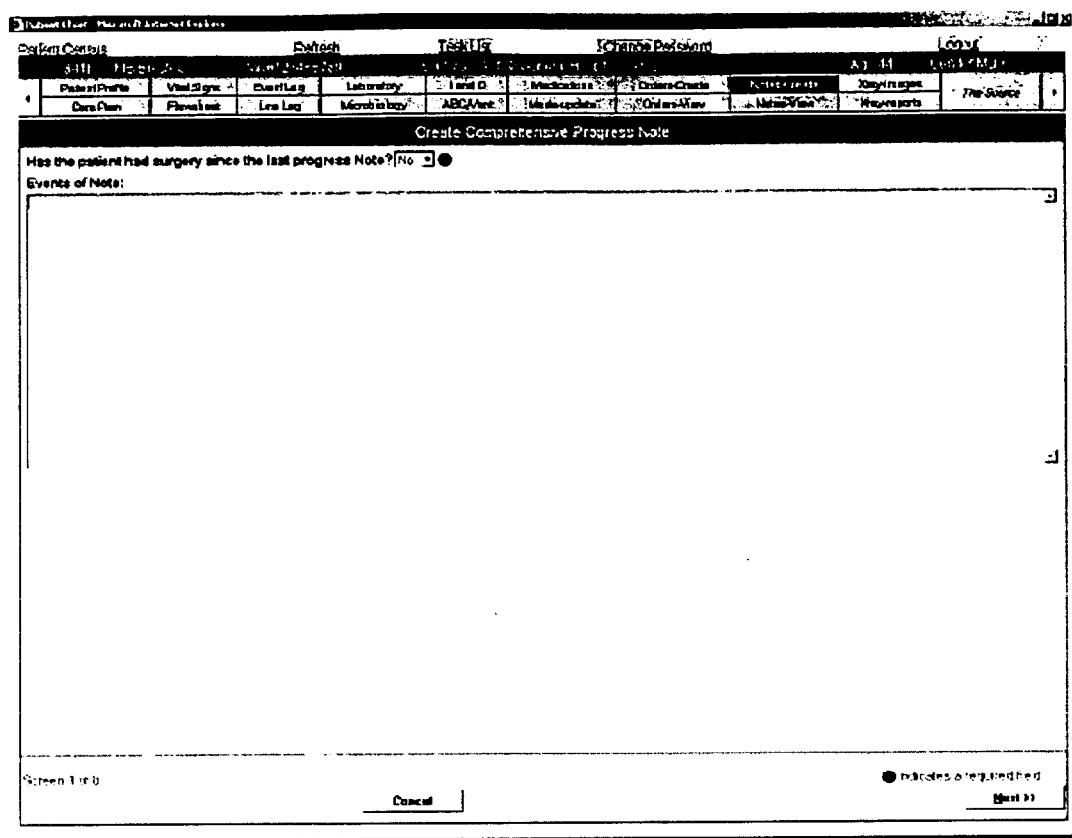
FIG. 18 illustrates events of screen note(s).

FIG. 13 illustrates data fields for data population of Laboratory Results. A user selects the lab results that are in the final note. To select the laboratory results to print, click the box next to the laboratory test type. Corresponding lab results will appear in the printed Note.

Assessment and Plan (Other Issues). A field is reserved for data entry in text from to record any additional Assessment and Plan information not previously captured by the pick lists.

Figure 14:
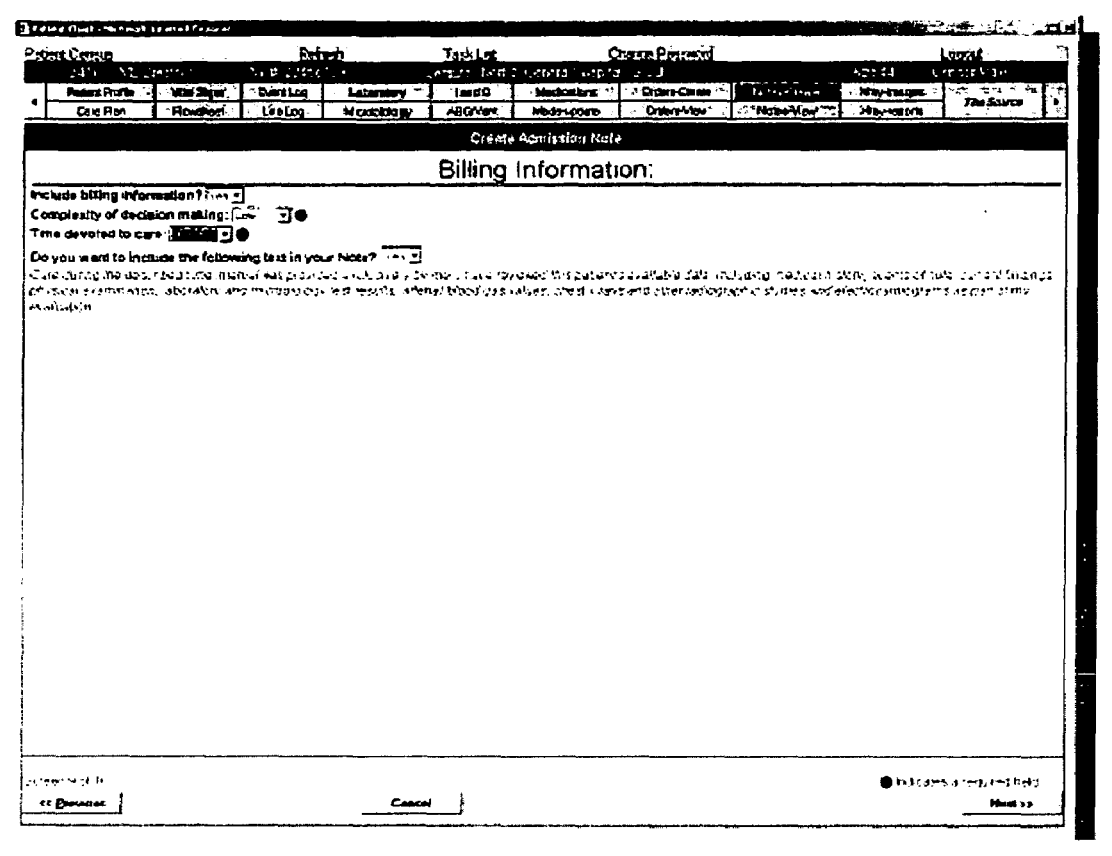

FIG. 14 illustrates the fields, Billing Information screen. A user enters billing information" and is presented with a pick list. If no billing information is entered, this data field is not populated and completes the screen.

Figure 15:
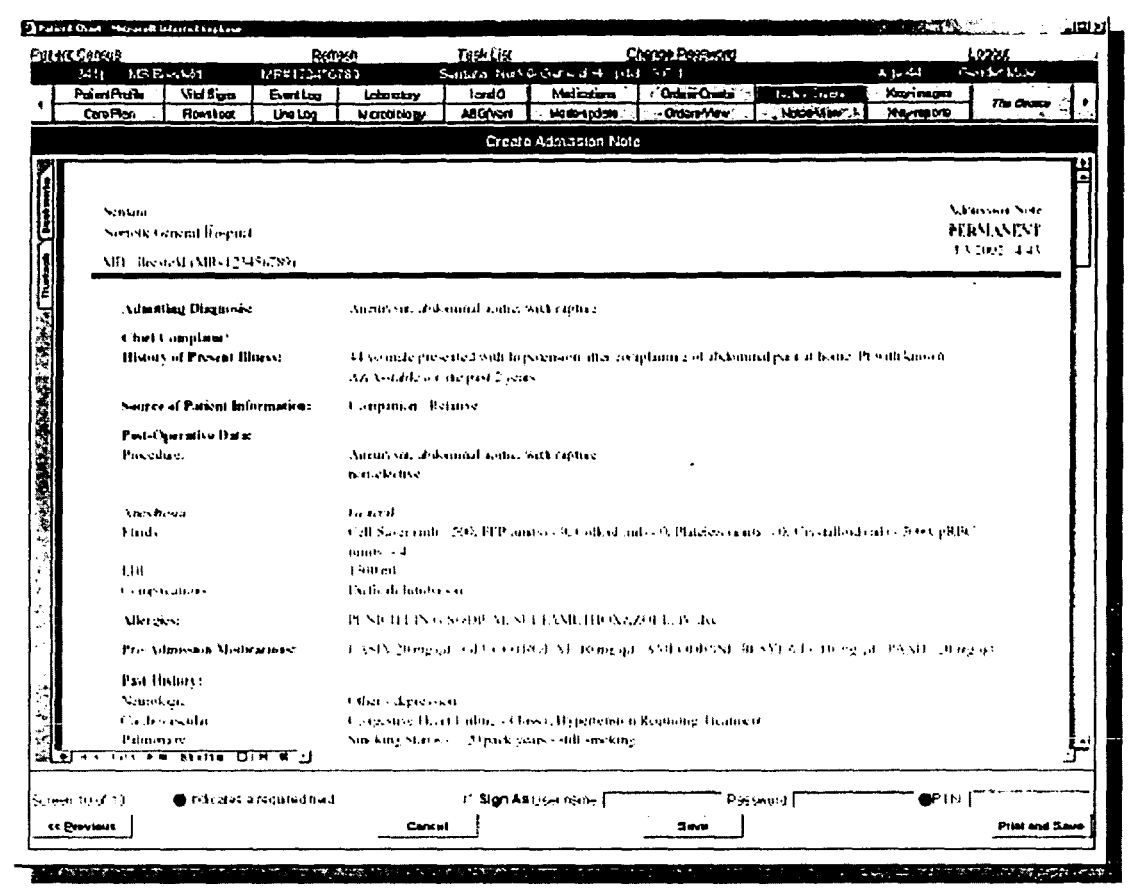

FIG. 15 illustrates an Admission Note. The Admission Note screen provides a user view, sign, and print options. The admission note must be signed before it can be saved or printed.

To sign a note and print the note in the ICU: a user must enter their P.I.N. and save button. To sign and save a note without printing, a user can sign a note that is entered under a different user's logon by entering a user's name, password, and authorized clinician's PIN.

Another aspect of the present invention is the management of patients who are readmitted to an ICU Facility. Another embodiment provides for a user to create a readmission note for a patient to be entered into the ICU. The Readmission Note consists of ten screens:
1. Reason for Readmission, Surgical information, Admission Diagnosis, Chief Complaint/History of Present Illness
2. Allergies, Preadmission Medications
3. Past History
4. Review of Systems
5. Social History and Family History
6. Physical Exam
7. Today's Problems/Diagnoses, Today's Treatments/Diagnostics
8. Laboratory Results, Assessment and Plan
9. Billing information
10. View/Sign/Print Note.

The patient is a surgical patient when entered from the O.R. or went to the O.R. within 4 hours from admission. When the patient is admitted from the O.R., the note displays a Surgical Admission Diagnosis and data fields in which to record relevant post-operative information. When the patient is not admitted from the O.R., the patient is a Medical Admission and a Medial Admission Diagnosis data field is displayed.

Another embodiment of the present invention is the Readmission note that can be either surgical or medical. Readmission Note (Medical) describes the procedures for creating a readmission note for a patient who was admitted to the ICU directly. Admission Note (Surgical) describes the procedures for creating a readmission note for a patient who was admitted to the O.R. before admission.

A readmission note for a patient who is not admitted to the O.R. before admission is a medical readmission note. The user enters an admitting Diagnosis with the Reason for Readmission from the pick list. The Admitting Diagnosis fields are selected from the pick lists. The program contains a data field for the Chief Complaint/History of Present Illness. The user selects the Source of Patient information from the pick list. When a readmission is via the O.R., the readmission is classified as surgical. To create a readmission note for a patient who was admitted to the O.R., before admission into the ICU, the user specifies that the patient is admitted from the O.R.

Figure 17:
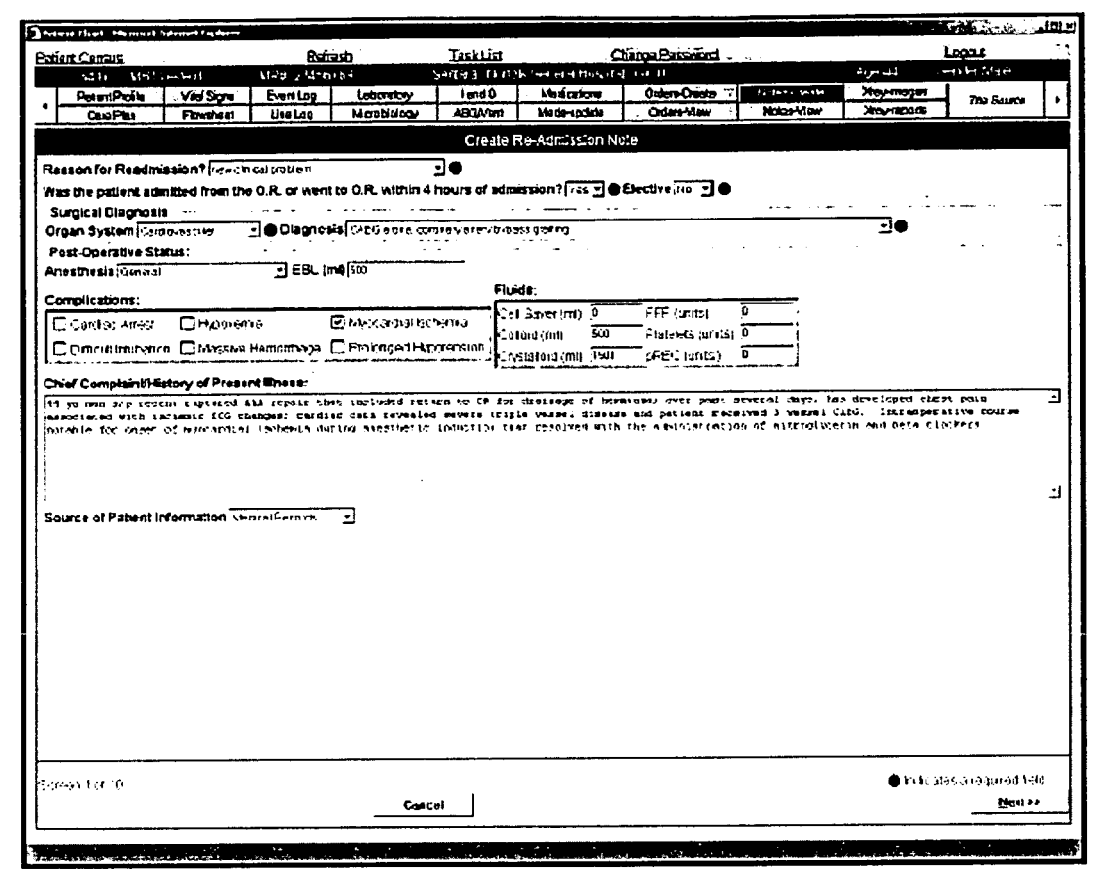

FIG. 17 illustrates a Surgical Diagnosis data field. The user enters data as to the diagnosis and selects options from the pick list to populate the remaining data fields. Data from the previous Admission note populates sub data fields in the surgical diagnosis screen. This can be edited if new information has been obtained since the last admission. The procedure for completing the sub data fields is the same as for the procedure for populating the Admission Note data fields.

A Comprehensive Progress Note data field is not available to a user until an Admission Note section is saved. The Comprehensive Progress Note consists of 8 data (screens): Within each Data field are sub data fields that require population with patient specific data:
1. Surgical Information, admission Diagnosis, Events of Note
2. Allergies, Preadmission Medications
3. Past History
4. Physical Exam
5. Today's Problems/Diagnoses, Today's Treatments/Diagnostics
6. Laboratory Results, Assessment and Plan
7. Billing Information
8. View/Sign/Print Note.

A Comprehensive Progress Note for new surgery data section provides instructions for creating a Comprehensive Progress Note for a patient who had surgery since the last Progress Note. There are a total of 8 screens in the readmission process A Comprehensive Progress Note created for a patient who was not admitted to the O.R. before admission.

Figure 19:
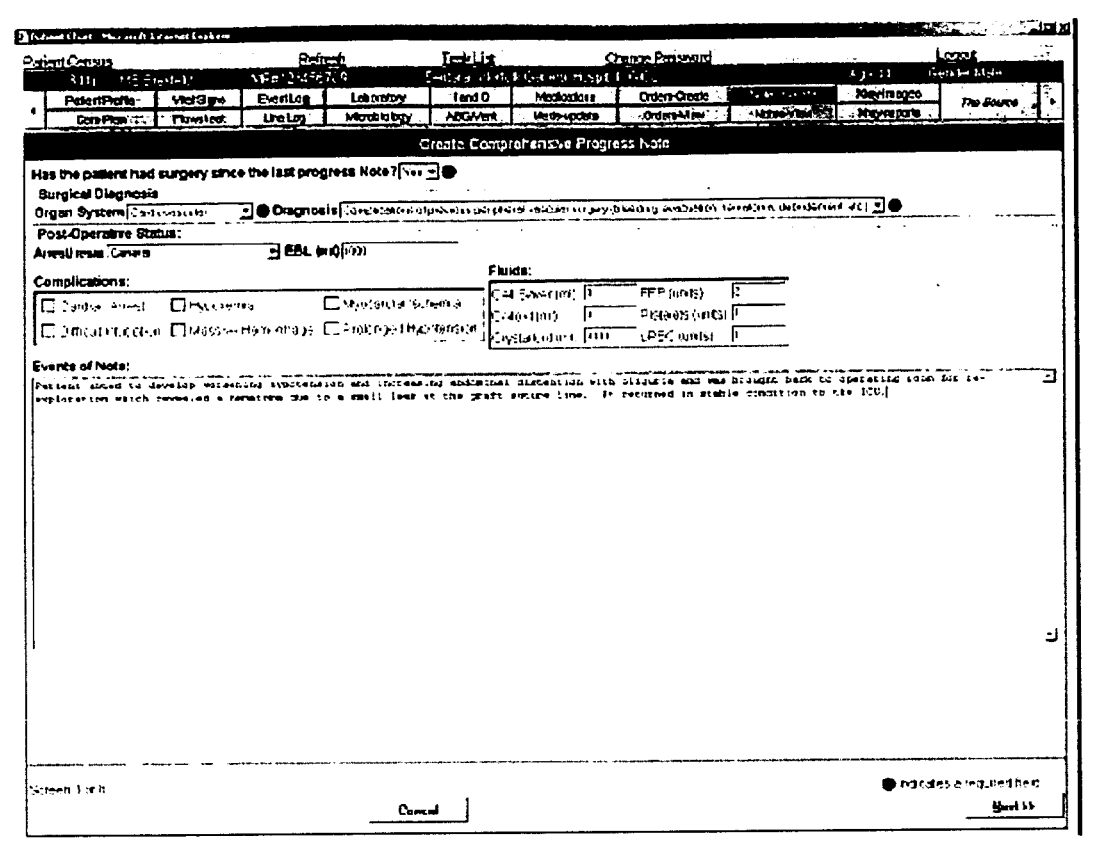

FIG. 19 illustrates a Comprehensive Progress Note data section. A user enters Events of Note information. The information entered when the Admission Note is created populates the same data fields in the Comprehensive Progress Note.

A Brief Progress Note provides the physician with a means of documenting changes in patient status, updates and interventions. The progress note consists of 3 data fields: 1. Surgery question, Events of Note 2. Today's problems/Diagnoses, Today's Treatments/Diagnostics 3. View/Sign/Print Note. A user uses a Brief Progress Note for creating notes for a patient who has not had surgery since the last Progress Note. A Medical Brief Progress Note is used for creating a Brief Progress Note for a patient who has had surgery since the last Progress Note.

To create a Brief Progress Note for a patient who has not had surgery since the last Progress Note. Selecting the Progress link and indicating that no surgery has taken place since the last progress note populates the surgery field. Data is Entered under Events of Note data field for random notes pertaining to the patient.

To create a Brief Progress Note for a patient who has had surgery since the last Progress Note: the user selects the Brief Progress link and enters data as to the necessary Post-Operative Status fields. Data as to Events of Note information is entered in the free form field.

Figure 20:
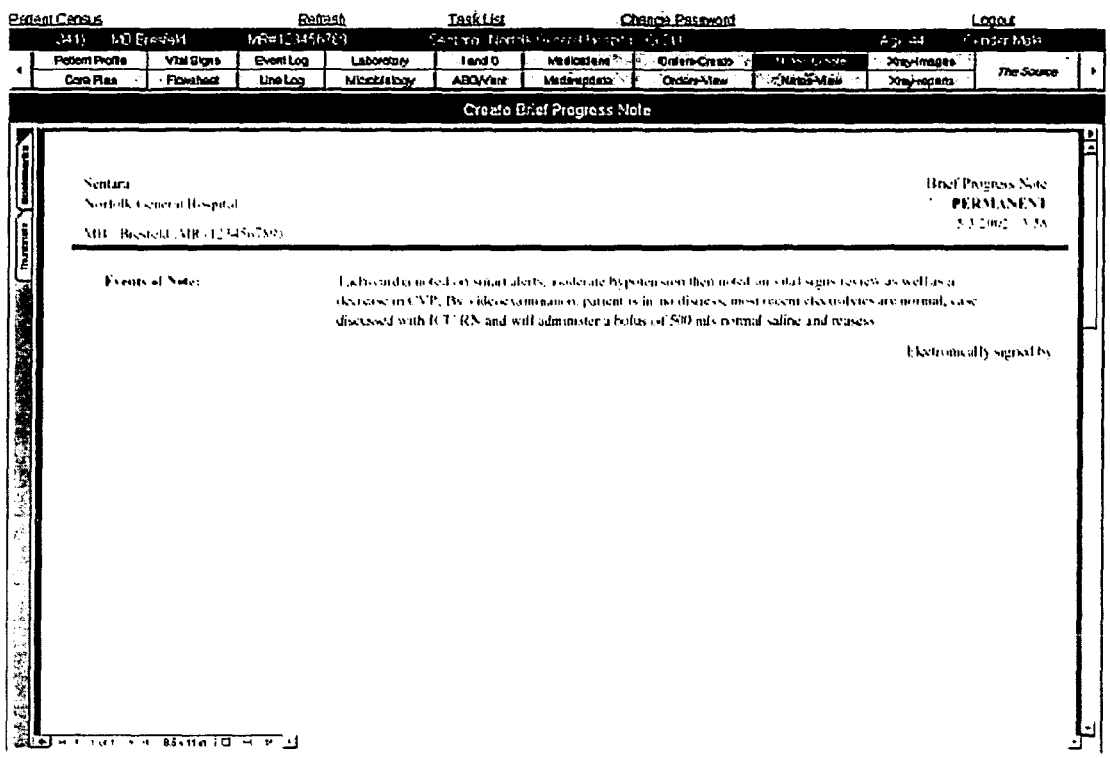
FIG. 20 illustrates brief progress note screen

FIG. 20 illustrates a Brief Progress Note screen. Modifications to data screens displayed on the Brief Progress note changes by navigating with the Previous button to go back to the screen(s) that require correction(s), making the necessary changes and advancing to the final screen. Thus the physician can change the active diagnosis and treatment based on the latest information about the patient. The Brief Progress Note is signed before it is saved or printed. By signing the note, the user authorizes updating the patient's chart with information from the Note.

A note is signed by the user by entering a P.I.N A user can sign a note that is entered under a different user's logon: using the Sign As entry and entering the user name followed by the password and the authorized clinician's P.I.N. in the sign field. When the Brief Progress Note is Completed and signed, you save the Admission note by clicking the Save button. Print and save the Brief Progress Note by clicking on the Print and Save button.

Figure 21:
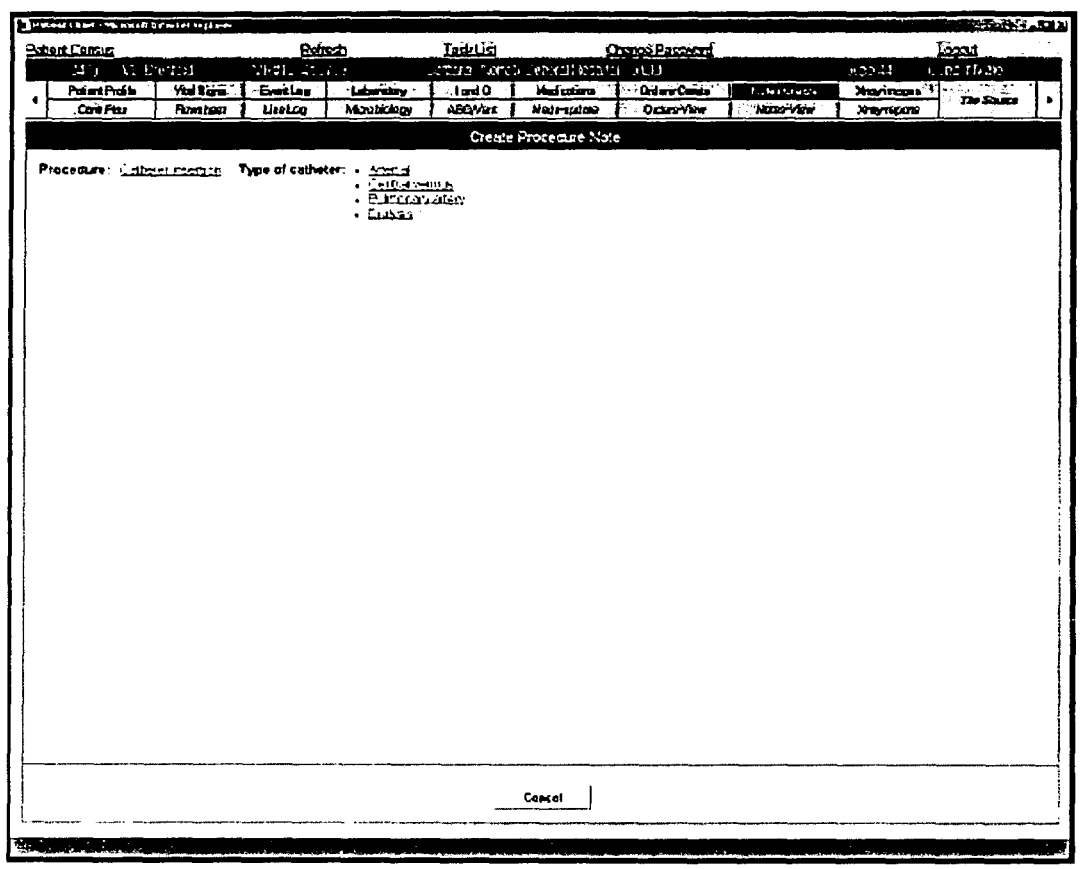
FIG. 21 illustrates a procedure screen.

FIG. 21 illustrates a Procedure Note providing the physician with a Means of tracking and documenting procedures that were performed on a patient. The Procedure Note consists of two screens: 1. Procedure 2. View/Sign/Save Note. To Create a Procedure Note: the user selects the Procedure link and selects a procedure from a pick list. The procedures are listed as links. When a procedure is selected, additional links are displayed.

A user can cancel the Procedure Note from any of the screens in the Create-Note process.

Figure 22:
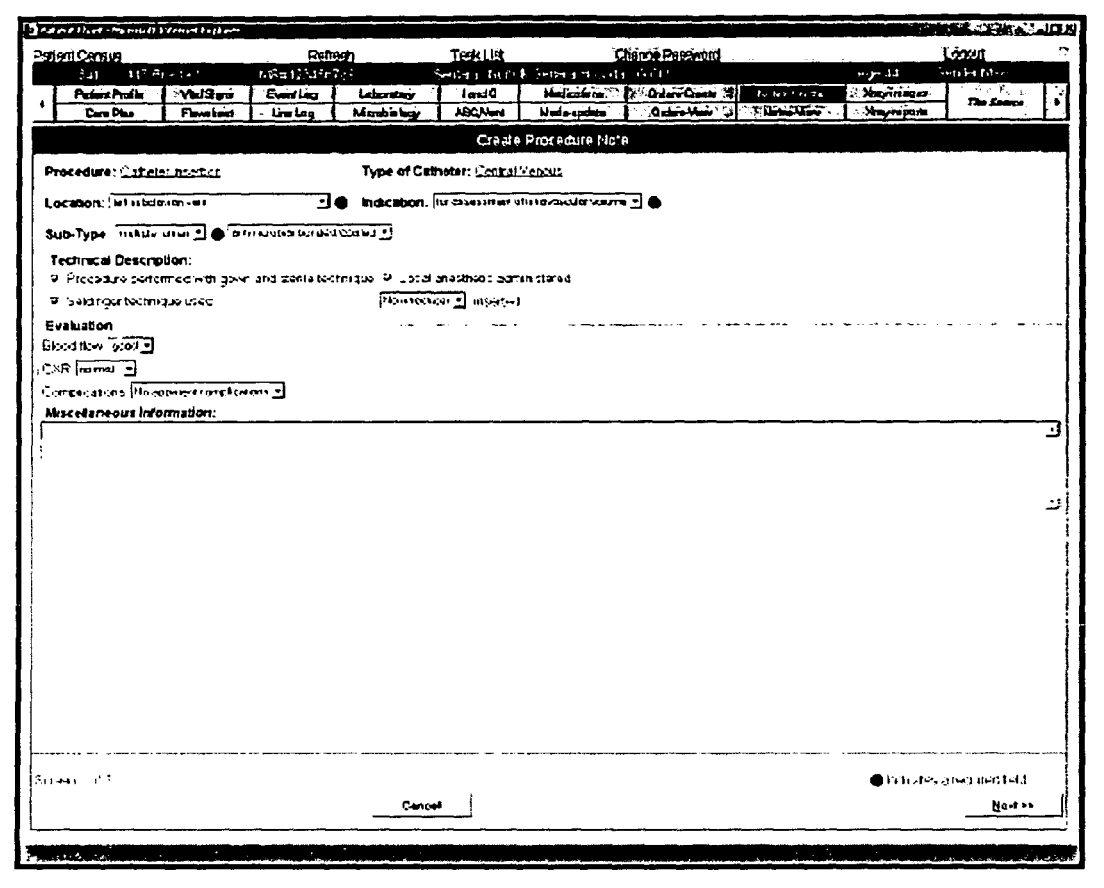

FIG. 22 illustrates Procedure Note Specifics screen. A user enters the information from the pick lists. For example, when a user selects catheter insert a pick list displays the types the types of catheters the facility provides that the user selects. This displays the Procedure Note Final screen.

Figure 23:
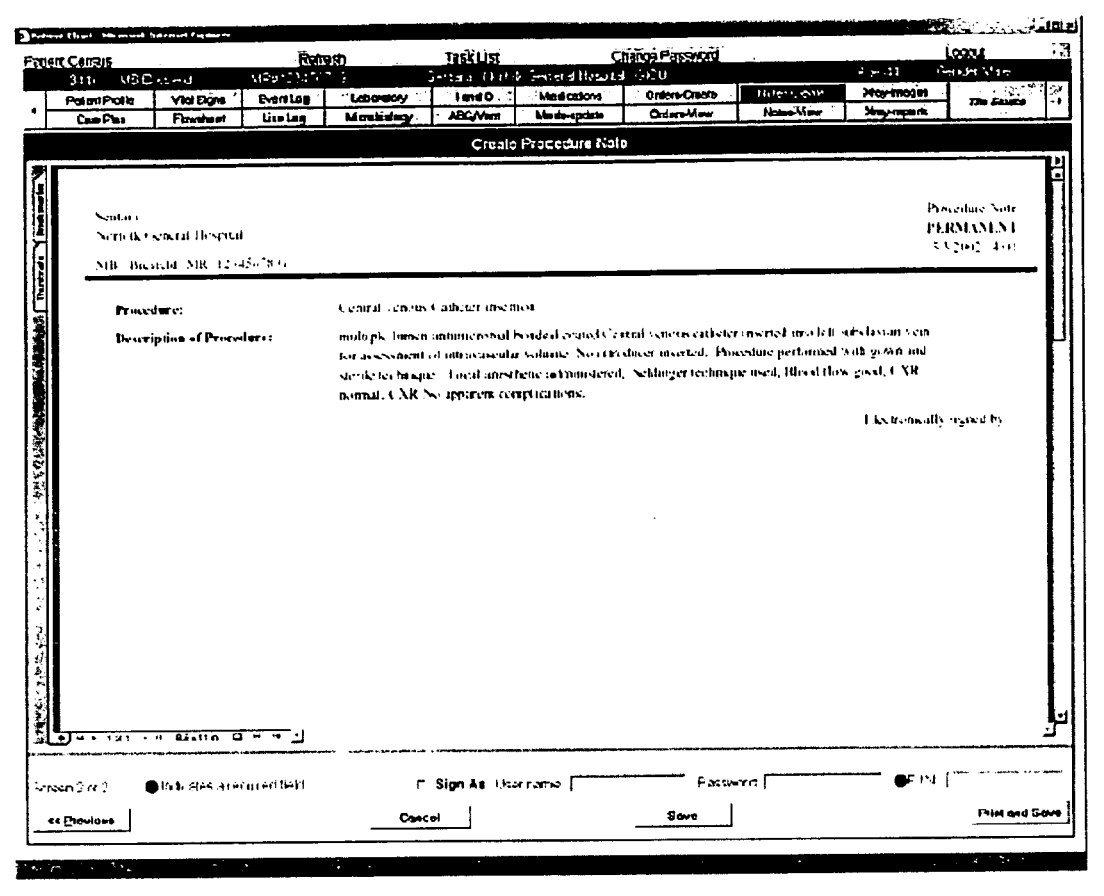

FIG. 23 illustrates a Procedure Note Final screen. To make modifications to previous screens: the user selects the Previous button to go back to the screen(s) that require corrections (s). The user makes the necessary changes and advances to the final screen of the Procedure Note. Sign. By signing the note, the user authorizes updating the patient's chart with information from the note. Once this occurs, the present invention populates the various files that require such information such as billing systems, line logs, patient profile information and the like.

A user signs a Note by entering a P.I.N. To allow one user to sign a note that is entered under a different user's logon: the user checks the Sign As box and enters the user's name, password, and the authorized clinician's P.I.N. in the sign field. When the Procedure Note is completed and signed, the user saves the note by clicking on the Save button. The user may print and save the Procedure Note by clicking the Print and Save button. A prompt is displayed to "wait while the note is printed and saved." Another prompt notifies the user that "Your note has been printed and saved." The Notes—View button enables a user to view a completed note including the date/time of every note. A note set is numbered and dated in reverse chronological date order, displaying the most recent note first for easy reference.

Figure 24:
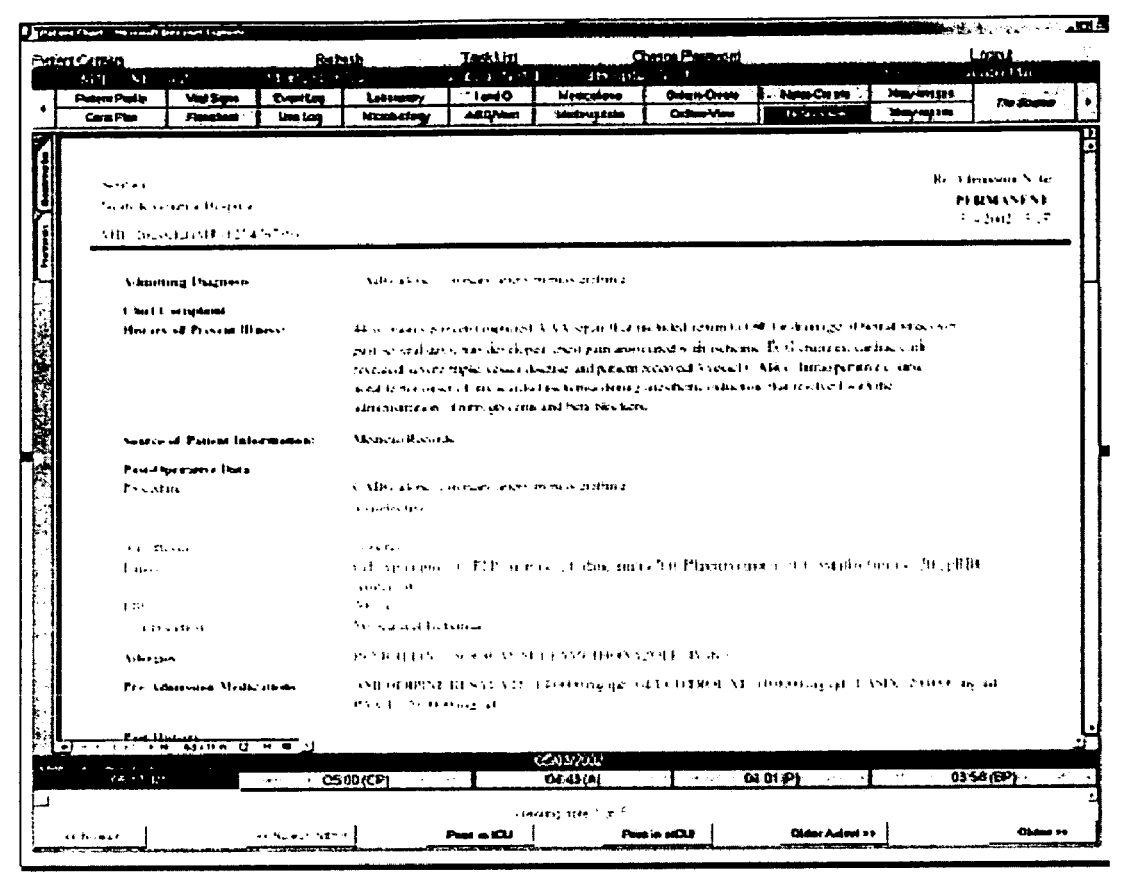

FIG. 24 illustrates a Notes View screen a user can view any note by clicking on the note's time. When more than one note is shown, the user may view other notes by selecting the note to be viewed. The Note can be printed in the hospital, ICU, or the eICU facility. Notes that have been created and saved are displayed by time (newest to oldest) at the bottom of the Notes—view screen. The time is followed by letters that identify the type of note. These abbreviations are used: A—admission Note R—Readmission Note P—Procedure Note CP—Comprehensive Progress Note BP—Brief Progress Note As mentioned previously, the note writing application of the present invention is designed to capture clinical patient information for reuse within the patient care system. The following examples illustrate several ways in which present invention utilizes the data stored during physician note writing:

Physician-entered data are populated within patient care system in order to place information in a context that facilitates patient assessment and monitoring. These data are often displayed with information obtained from other sources (or other notes), with the goal to portray patient information in a format that highlights temporal and contextual relationships and helps physicians detect patterns that may otherwise not be appreciated. Examples include the creation/maintenance of the Line Log from physician procedure notes and the display of active diagnoses and treatments on a Patient Profile.

Physician-entered data (active diagnoses and past history) automatically configures "smart" diagnostic systems for specific patients. Examples include the automatic selection of more sensitive default thresholds for heart rate alarms in patients at risk for or suffering from active coronary heart disease and the identification of high-acuity patients without specified preferences for end-of-life support.

Physician notes entered using the present invention are used to determine physician adherence to best practices and are used in reporting on patient care. Examples of such adherence that may be reported include the use of mechanical compression devices to prevent deep venous thrombosis, the detection of contraindications to the use of beta blockers, the presence of risk factors that increase predicted mortality, and many others.

The capture of this granular, time-stamped information through the physician note writing system of the present invention therefore facilitates the use and administration other patient care devices and systems.

It is also important to note that many of the physician notes are nested within data categories. Thus, information that is germane to a diagnosis or administrative function can be obtained readily depending on how the much a hospital personnel needs to "drill down" through such data. For example, it may be necessary for a physician to know that a patient has pneumonia AND to know the type of bacteria causing the pneumonia. However, a billing administrator need only know that the diagnosis is pneumonia. Other information about the specific pathogen causing the condition is NOT required. Further the present invention will provide only that information that is germane to the function being performed. Thus the billing administrator will not normally get the same information that the physician would receive, but only that which is necessary to do the administrative job.

In another embodiment of the present invention, information that is acquired is used for severity-adjustment scoring of patient illness. By way of illustration and not as a limitation, information gathered by the present invention is used to determine an APACHE II score (which is well-known in the art). The APACHE II score is a general measure of disease severity based on current physiologic measurements age and previous health condition. The score can help in the assessment of patients to determine the level and degree of diagnostic and therapeutic intervention. Included in the score are values associated with acute physiology, age, and chronic health.

In yet another embodiment of the present invention, data automatically configures "smart" diagnostic systems that provide the information for completion of the APACHE assessment. The same smart diagnostic systems alert administrator if there is insufficient data to provide an assessment. As will be apparent to those skilled in the art, other severity-adjustment assessment tools may be used with embodiments of the present invention without depart from its scope.

Although the present invention has been described in terms of specific embodiments, various substitutions of materials and conditions can be made as will be appreciated by those skilled in the art. Further, while critically ill patients substantially benefit form the functions of the physician note writing applications of the present invention; this is not meant as a limitation. The present invention will find uses throughout the patient care system whether the patient is critically ill or receiving more "routine" medical care. Thus the description contained herein should be applied to all levels of patient care, whether the patient is in an institution for several days or is receiving outpatient care. In addition, the creation of physician notes need not occur at a fixed station. The templates for entering physician note information can be installed on portable computers, on PDA's as well as on more standard computer terminals found in hospitals. Similarly, a physician does not have to be "wired" to the servers of the present invention since the present invention can equally function in a wireless environment with physician PDA's or the like communicating in a wireless fashion with the patient care system. Thus the scope of the invention is only to be limited by the following claims.

What is claimed is:

1. A method for utilizing physician notes in a healthcare system comprising:
   inputting patient health data reflecting a current state of patients in geographically dispersed health care locations and treatment objectives for the patients to an input device, wherein the patient health data is inputted via formatted input options presented by the input device and wherein the input device is connected to a network;
   receiving the patient health data in the healthcare system via the network;
   monitoring patient data elements of the patients;
   communicating the monitored patient data elements from the geographically dispersed health care locations to a remote command center via the network, wherein the remote command center comprises a database;
   storing the monitored patient data elements in the database, wherein the database comprises stored patient data elements;
   creating a rule for a patient using the patient health data and the patient data elements;
   applying the rule continuously to selected patient data elements stored in the database to search for patterns of data and to produce an output indicative of a change in a medical condition of the patient; and
   utilizing the output to determine if intervention is warranted,
   wherein the monitoring and determining if intervention is warranted for the patient occurs in an automated fashion at the remote command center 24 hours per day 7 days per week.

2. The method for utilizing physician notes in a healthcare system of claim 1, wherein inputting patient health data comprises inputting data on remote devices selected from the group consisting of wired devices and wireless devices.

3. The method for utilizing physician notes in a healthcare system of claim 1, wherein inputting patient health data reflecting the current state of the patients comprises:
   selecting a note template;
   selecting a structured data element associated with the selected template, wherein the selected structured data element is indicative of the current state of the patient and the treatment objectives for the patient, and incorporating the selected structured data element into the selected note template to create a completed template;
   associating the completed template with the patient; and
   releasing the completed template to the healthcare system.

4. The method for utilizing physician notes in a healthcare system of claim 3, wherein receiving the patient health data in the healthcare system comprises:
   time stamping the patient health data when it is released to the healthcare system; and
   storing the time stamped patient health data in a datastore accessible to remote command center.

5. The method for utilizing physician notes in a healthcare system of claim 1, wherein the patient rule comprises an algorithm.

6. The method for utilizing physician notes in a healthcare system of claim 1, wherein the selected patient data elements comprise a physiological data element of the patient and a clinical data element of the patient.

7. The method for utilizing physician notes in a healthcare system of claim 1, wherein the selected patient data elements comprise a physiological data element of the patient and a medication data element of the patient.

8. The method for utilizing physician notes in a healthcare system of claim 1, wherein the selected patient data elements comprise a physiological data element of the patient and a laboratory data element of the patient.

9. The method for utilizing physician notes in a healthcare system of claim 1, wherein the selected patient data elements comprise a clinical data element of the patient and a laboratory data element of the patient.

10. The method for utilizing physician notes in a healthcare system of claim 1, wherein the selected patient data elements comprise a physiological data element of the patient and another physiological data element of the patient.

11. The method for utilizing physician notes in a healthcare system of claim 1, wherein the selected patient data elements comprise at least two data elements of the patient selected from the group consisting of a physiological data element, a clinical data element of the patient, a medication data element of the patient, and a laboratory data element of the patient.

12. The method for utilizing physician notes in a healthcare system of claim 1, wherein the patient data elements are selected from the group consisting of physiological data elements and clinical data elements.

13. The method for utilizing physician notes in a healthcare system of claim 1, wherein the output indicative of the change in the medical condition of the patient comprise data indicative of degradation of the condition of the patient.

14. A system for utilizing physician notes in a healthcare system comprising:
   a network;
   an input device connected to the network, wherein the input device comprises instructions for:
      presenting formatted input options; and
      receiving patient health data reflecting a current state of patients in geographically dispersed health care locations and treatment objectives for the patients in accordance with the formatted input options;
   monitoring stations comprising monitoring equipment comprising instructions for monitoring data elements from patients in the geographically dispersed healthcare locations and sending the monitored data elements to a remote command center via the network, and wherein the remote command center comprises:
      a database, wherein the database comprises stored patient data elements relating to the patients;
      a computerized patient care management system, wherein the computerized patient care management system comprises instructions for:
      receiving the monitored patient data elements from the plurality of geographically dispersed health care locations;
      storing the monitored patient data elements in the database;
      creating a rule for a patient using the patient health data and the patient data elements;
      applying the rule continuously to selected patient data elements stored in the database to search for patterns of data and to produce an output indicative of a change in a medical condition of the patient; and
      utilizing the output to determine if intervention is warranted, wherein the monitoring and determining if intervention is warranted for the patient occurs in an automated fashion at the remote command center 24 hours per day 7 days per week.

15. The system of claim 14, wherein the patient health data input device comprises devices selected from the group consisting of wired devices and wireless devices.

16. The system of claim 14 wherein the healthcare system further comprises structured data elements stored in a datastore accessible to users of the healthcare system, and wherein the healthcare system further comprises instructions for:
completing and releasing applicable structured data elements; and
making the released structured data elements accessible to a user having access to the datastore;
time stamping the patient health data when it is release by a physician; and
storing the time stamped patient health in the datastore.

17. The system of claim 14, wherein the patient rule comprises an algorithm.

18. The system of claim 14, wherein the selected patient data elements comprise a physiological data element of the patient and a clinical data element of the patient.

19. The system of claim 14, wherein the selected patient data elements comprise a physiological data element of the patient and a medication data element of the patient.

20. The system of claim 14, wherein the selected patient data elements comprise a physiological data element of the patient and a laboratory data element of the patient.

21. The system of claim 14, wherein the selected patient data elements comprise a clinical data element of the patient and a laboratory data element of the patient.

22. The system of claim 14, wherein the selected patient data elements comprise a physiological data element of the patient and another physiological data element of the patient.

23. The system of claim 14, wherein the selected patient data elements comprise at least two data elements of the patient selected from the group consisting of a physiological data element, a clinical data element of the patient, a medication data element of the patient, and a laboratory data element of the patient.

24. The system of claim 14, wherein patient data elements are selected from the group consisting of physiological data elements and clinical data elements.

25. The system of claim 14, wherein the output indicative of the change in the medical condition of the patient comprises an output indicative of degradation of the condition of the patient.

* * * * *